United States Patent [19]

VandenEinde et al.

[11] Patent Number: 5,415,639
[45] Date of Patent: May 16, 1995

[54] SHEATH AND METHOD FOR INTRAVASCULAR TREATMENT

[75] Inventors: David A. VandenEinde, Minneapolis; Peter T. Keith, Fridley; Daniel O. Adams, Orono; Robert E. Atkinson, St. Anthony, all of Minn.

[73] Assignee: SciMed Life Systems, Inc., Maple grove, Minn.

[21] Appl. No.: 45,019

[22] Filed: Apr. 8, 1993

[51] Int. Cl.⁶ .............................................. A61M 25/00
[52] U.S. Cl. ................................... 604/283; 604/102; 604/164
[58] Field of Search .................. 604/160, 161, 96, 95, 604/102, 280, 282, 283, 164, 264; 606/192, 194; 128/772, 656–658

[56] References Cited

U.S. PATENT DOCUMENTS

| | | | |
|---|---|---|---|
| 4,771,777 | 9/1988 | Horzewski et al. | 604/102 |
| 4,798,193 | 1/1989 | Giesy et al. | 128/7 |
| 4,932,413 | 6/1990 | Shockey et al. | 128/657 |
| 4,947,864 | 8/1990 | Shockey et al. | 128/772 |
| 4,968,300 | 11/1990 | Moutafis et al. | 606/194 |
| 4,988,356 | 1/1991 | Crittenden et al. | 606/192 |
| 5,069,673 | 12/1991 | Shwab | 604/282 |
| 5,102,403 | 4/1992 | Alt | 128/772 |
| 5,135,535 | 8/1992 | Kramer | 606/194 |
| 5,154,725 | 10/1992 | Leopold | 604/102 |
| 5,167,634 | 12/1992 | Corrigan, Jr. | 604/160 |
| 5,171,222 | 12/1992 | Euteneuer et al. | 604/102 |
| 5,195,978 | 3/1993 | Schiffer | 604/161 |
| 5,201,723 | 4/1993 | Quinn | 604/282 |
| 5,205,822 | 4/1993 | Johnson et al. | 604/180 |
| 5,234,407 | 8/1993 | Teirstein et al. | 128/772 |
| 5,242,396 | 9/1993 | Evard | 606/194 |
| 5,263,928 | 11/1993 | Trauthen et al. | 128/772 |
| 5,263,932 | 11/1993 | Jang | 604/102 |
| 5,267,958 | 12/1993 | Buchbinder et al. | 606/194 |
| 5,281,203 | 1/1994 | Ressemann | 604/164 |
| 5,290,247 | 3/1994 | Crittenden | 604/171 |
| 5,324,269 | 6/1994 | Miraki | 604/160 |
| 5,334,147 | 8/1994 | Johnson | 604/160 |

FOREIGN PATENT DOCUMENTS

| | | |
|---|---|---|
| WO92/15357 | 9/1992 | European Pat. Off. |
| 0397357 | 11/1990 | WIPO |
| 9222345 | 12/1992 | WIPO ............ 604/102 |

OTHER PUBLICATIONS

"A New Minicatheter and Deflector Technique for Renal Angioplasty," Hawkins, Jr., *Radiology* 145:837–838, Dec. 1982.

"The Cordis Shuttle Catheter," Cordis Corporation brochure, Dec. 1990, 2 pages.

*Primary Examiner*—C. Fred Rosenbaum
*Assistant Examiner*—Mark Bockelman
*Attorney, Agent, or Firm*—Kinney & Lange

[57] ABSTRACT

A sheath for facilitating a guide wire exchange is defined by an elongated tubular member having a proximal end, a distal end and a single thru lumen. The sheath also has a proximal insertion opening and a distal insertion opening in communication with the thru lumen. The sheath includes a distal guide segment for "single operator" insertion and a peelable extent for peelably removing the sheath after use. The distal guide segment is formed along a distal portion of the elongated tubular member. The sheath is inserted along a pre-inserted guide wire by inserting a proximal end of the pre-inserted guide wire through a guide lumen of the distal guide segment. The sheath is advanced distally along the pre-inserted guide wire to a desired position and thereafter the pre-inserted guide wire is withdrawn. A re-shaped guide wire or substitute guide wire is inserted through the proximal insertion opening and advanced through the thru lumen of the sheath to a treatment site. The sheath is withdrawn while peelably removing the tubular member from the inserted guide wire.

25 Claims, 12 Drawing Sheets

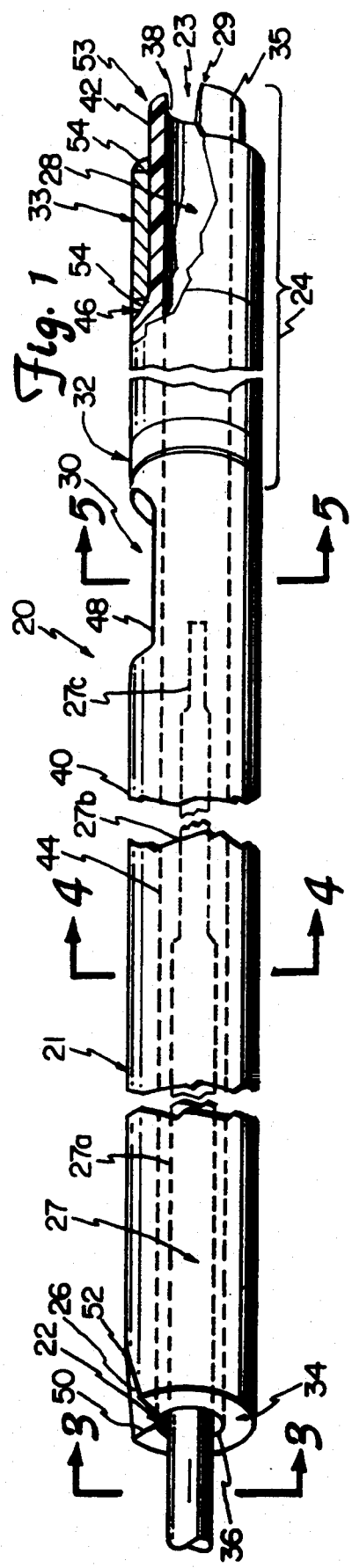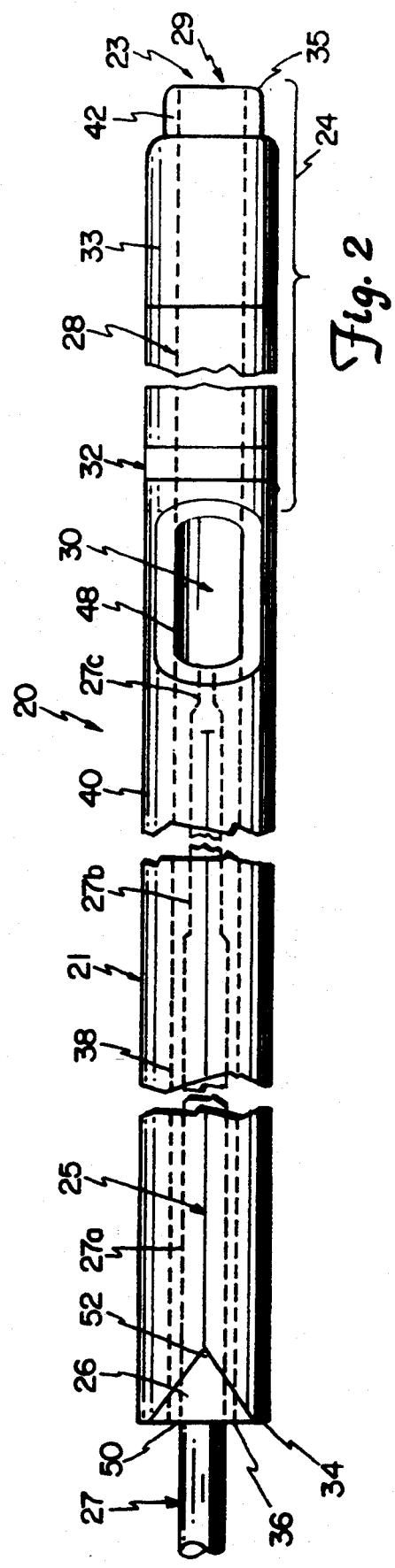

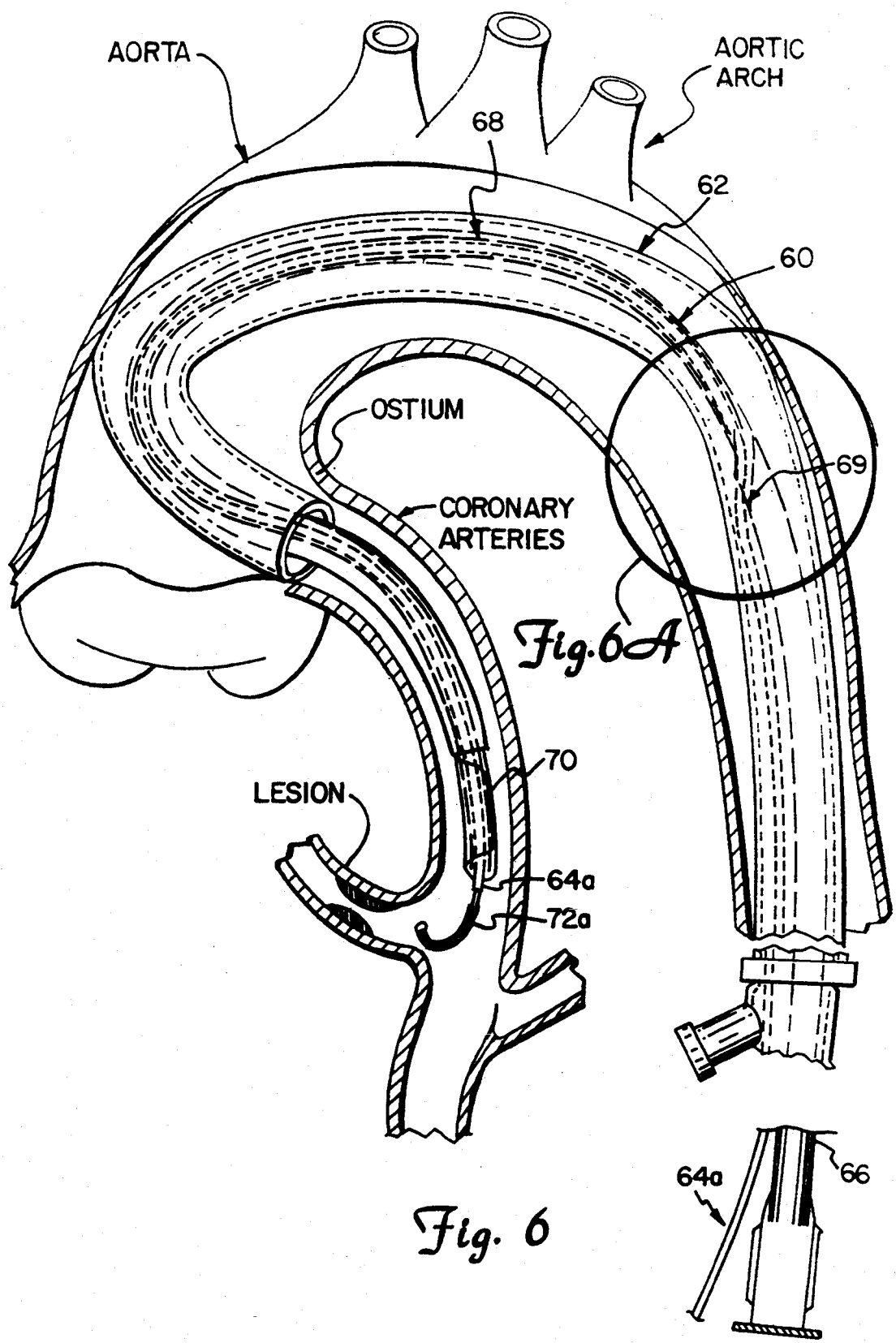

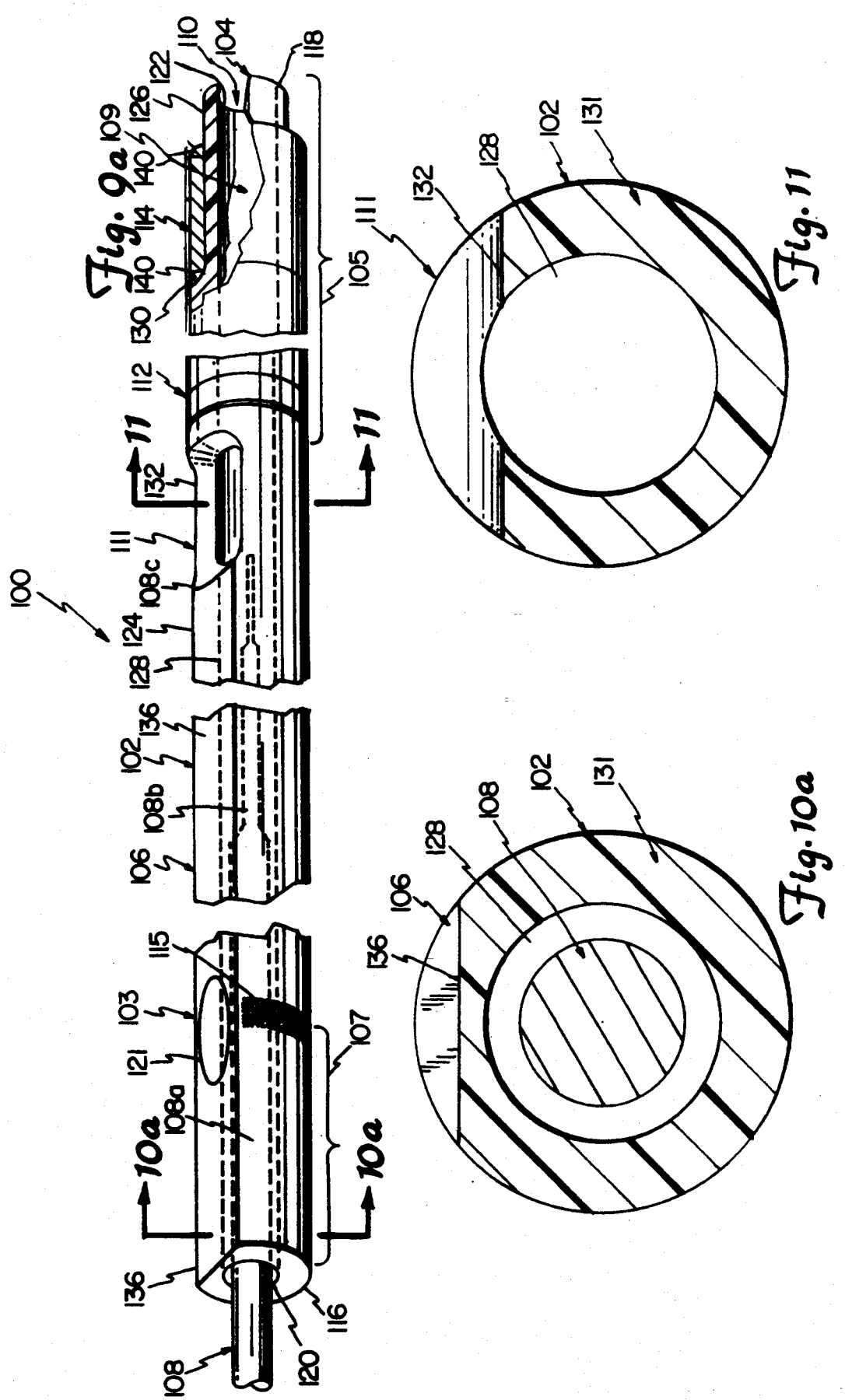

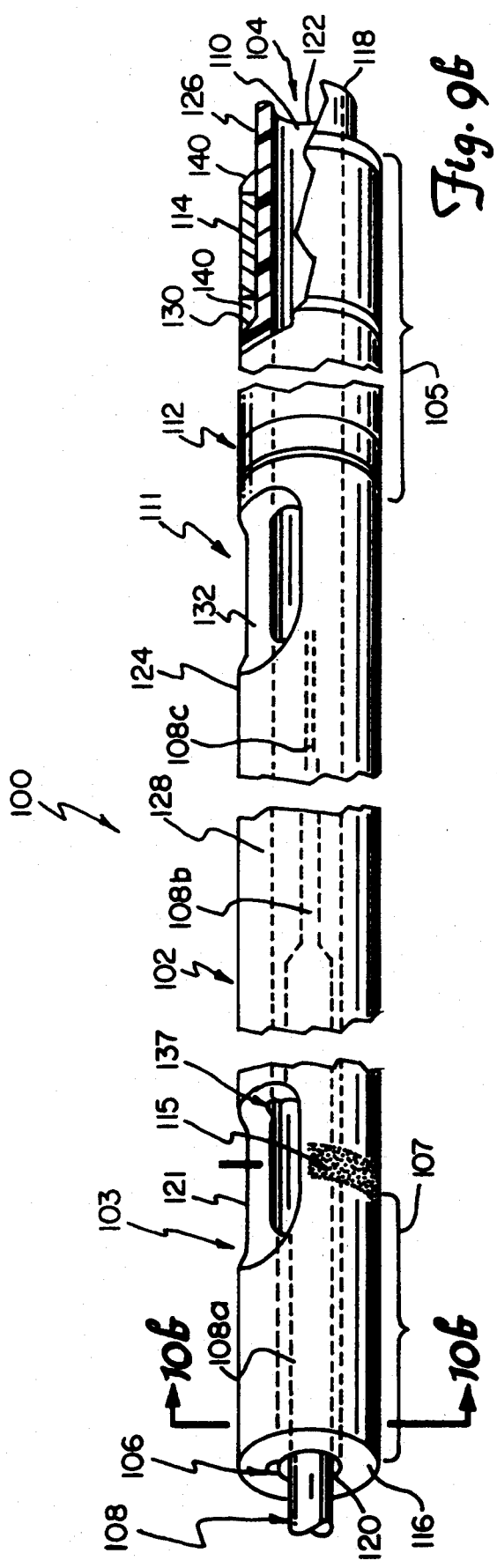
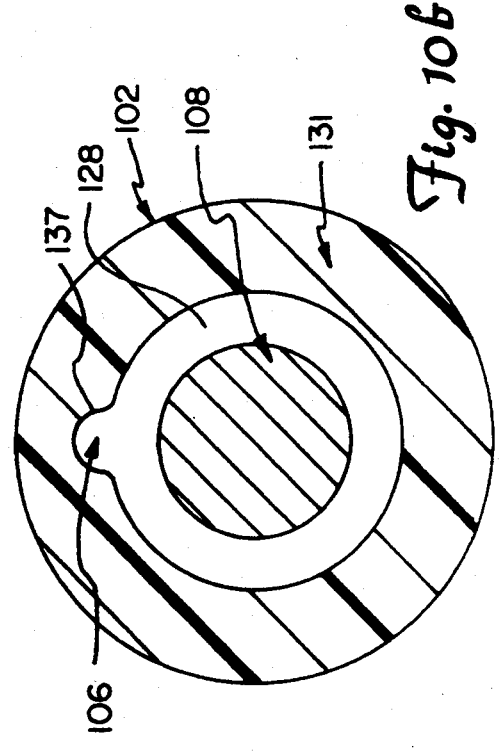

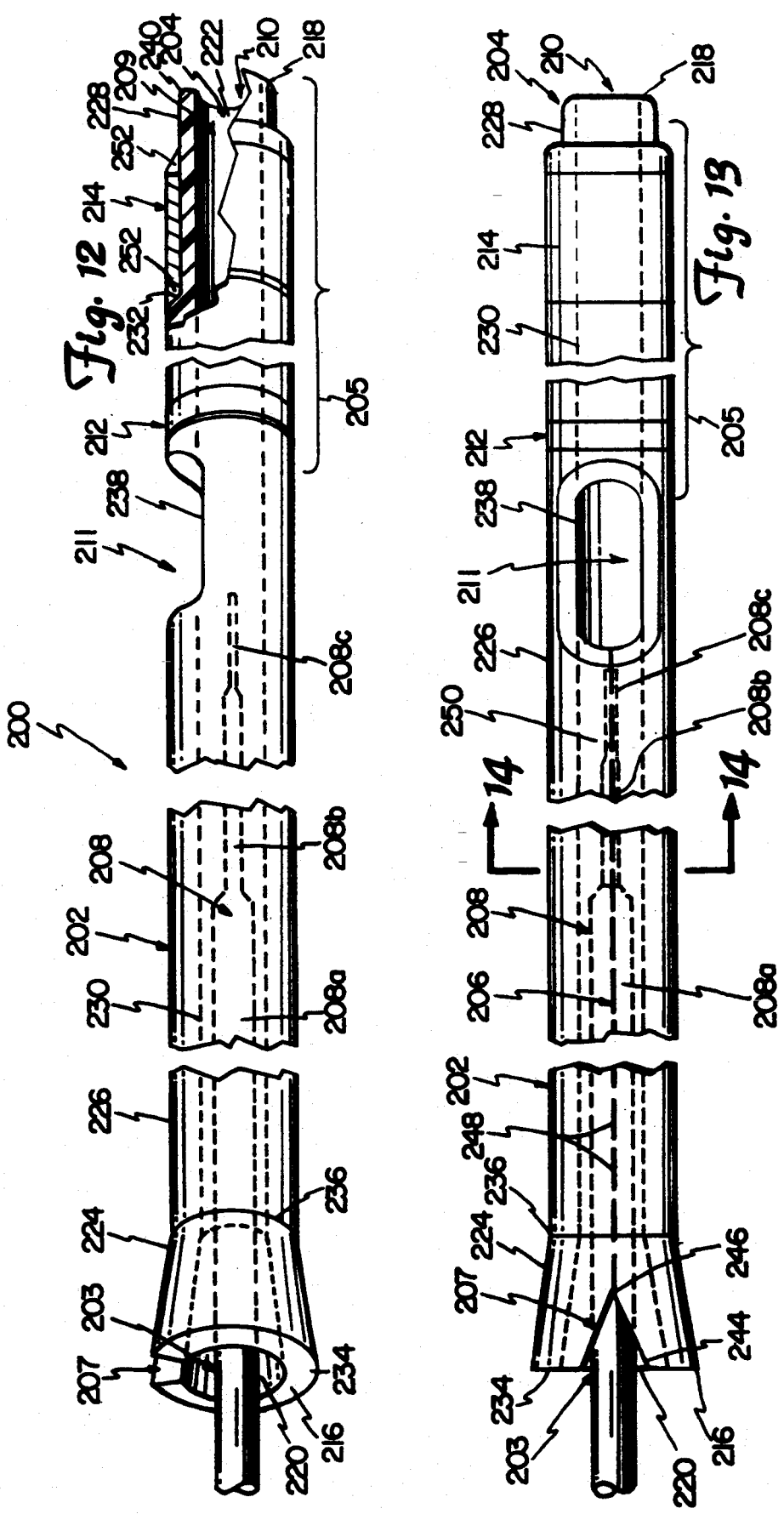

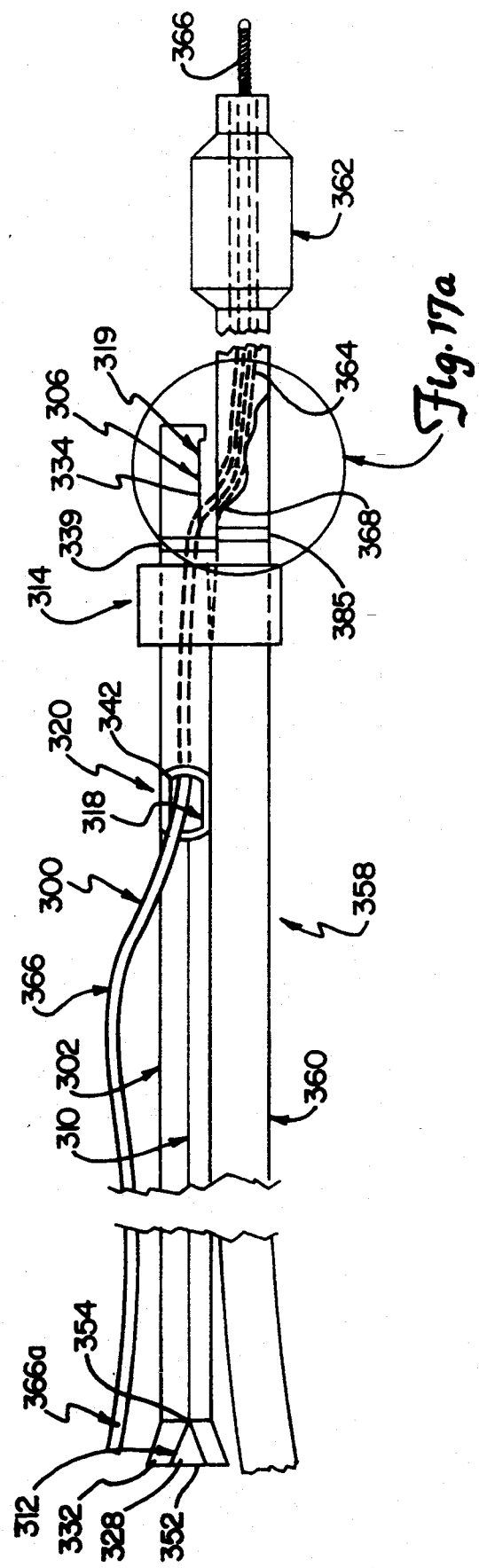

SHEATH AND METHOD FOR INTRAVASCULAR TREATMENT

BACKGROUND OF THE INVENTION

The present invention relates to a method and device used in intravascular therapeutic and diagnostic procedures and in particular to a method and device for use in facilitating a guide wire exchange.

Intravascular therapeutic and diagnostic techniques have developed, such as angioplasty, for treating certain vascular diseases. These techniques are an alternative to surgery and have proved quite successful. These techniques are particularly useful for treating certain types of coronary heart disease.

Therapeutic or diagnostic devices used to treat vascular diseases are typically formed of an elongated tubular member designed to extend from outside the patient through the vasculature of a patient to a treatment site. Some therapeutic or diagnostic intravascular devices (e.g., Percutaneous Transluminal Coronary Angioplasty ("PTCA") balloon catheters) are designed for use and insertion in combination with a steerable guide wire ("over-the-wire" type intravascular devices). Over-the-wire type devices include a guide wire lumen through which the guide wire is inserted for use in advancing the device to a treatment site.

A guide wire is designed to extend to a treatment site while a portion of the guide wire remains outside the patient for control. A distal tip portion of the guide wire typically is formed of a flexible construction. The flexible tip construction allows the operator to shape the distal tip and therefore navigate tortuous anatomy. An operator forms a bend on the distal tip to facilitate insertion and advancement of the guide wire so that the guide wire may be steered to the treatment site through the patient's vasculature.

The formed distal tip of a guide wire is sometimes discovered to be inappropriately shaped so that it is difficult to steer the guide wire to the treatment site, thereby making it extremely difficult for the operator to advance the intravascular device over the guide wire to the treatment site. Or, the distal tip of a pre-inserted guide wire may have been appropriate to track the guide wire to a first lesion but the distal tip is inappropriate to track to a second lesion requiring treatment. Accordingly, it is then necessary to withdraw the original guide wire to reshape its distal tip or substitute an alternately shaped guide wire therefor.

Alternatively, the guide wire inserted may be discovered to be too stiff or too flexible and it may be desirable to substitute a different guide wire with different properties. This procedure of withdrawing a guide wire previously inserted into a patient and reinserting a reshaped guide wire or a substitute guide wire is referred to as a "guide wire exchange."

In some "over-the-wire" intravascular device constructions, the guide wire lumen extends the entire length of the intravascular device so that a proximal opening to the guide wire lumen is positioned outside of the patient. Accordingly, if a guide wire exchange is necessary in a situation where the intravascular device and guide wire are already in place adjacent the treatment site in the patient's vasculature, the guide wire is withdrawn from the guide wire lumen of the device and a substitute guide wire is inserted through the exposed proximal opening of the guide wire lumen and advanced to a treatment site. Since the guide wire lumen extends along the entire length of the device, the substitute or reshaped guide wire is directed by the guide wire lumen through the vasculature of the patient to a treatment site.

Alternate "over-the-wire" device constructions have a guide wire lumen which does not extend along the entire length of the device. These devices are sometimes referred to as "single operator exchange" devices. The guide wire lumen of a "single operator exchange" device extends only along a distal portion of the device such that the proximal opening to the guide wire lumen is inside the patient when the device is inserted into the patient to a treatment site.

In such a device, like the Express ® balloon catheter made by SciMed Life Systems, Inc. of Maple Grove, Minn., a guide wire exchange is virtually impossible without moving the device proximally out of the patient to expose the proximal opening of its guide wire lumen. If the device is left in place in the patient and only the initially inserted guide wire is removed, it is extremely difficult, if not impossible, to locate and re-insert a reshaped or substitute guide wire into the small proximal opening of the "single operator exchange" device (which is not exposed outside the patient). Thus, when the initial guide wire for the device is removed, an operator is unable to maintain the device in position for inserting a reshaped or substitute guide wire into the patient for further treatment. Accordingly, the physician must retrace the entire tortuous path through the patient to the treatment site to reinsert a guide wire for treatment (which can be time consuming).

Revised catheter constructions or other devices have been proposed to allow a guide wire exchange when using a "single operator exchange" device. Such arrangements are shown, for example, in Kramer, U.S. Pat. No. 5,135,535 and Shockey et al., U.S. Pat. Nos. 4,932,413 and 4,947,864. In these examples, modification of the "single operator exchange" device is required or simultaneous control of multiple wires within the patient at times during the guide wire exchange procedure is required. Another approach to allow the exchange of a guide wire in a single operator exchange device is shown in copending U.S. patent application Ser. No. 07/725,064, filed Jul. 5, 1991, entitled "Guide Wire Sheath Method and Apparatus for Single Operator Exchange Catheter or Similar Device" (Ressemann), and which is owned by the assignee of the instant application (SciMed Life Systems, Inc. of Maple Grove, Minn. ) and incorporated by reference herein in its entirety. In this arrangement, a guide wire sheath extends over the guide wire and through the guide wire lumen of the device. Thus, when a guide wire exchange is performed, the sheath retains the path for the guide wire from outside the patient into and through the guide wire lumen of the single operator exchange device.

SUMMARY OF THE INVENTION

The present invention relates to a sheath for facilitating guide member exchanges. The sheath is formed of an elongated tubular member having a single longitudinally extending lumen sized to slidably receive a guide member therein. The tubular member includes a proximal insertion opening and a distal insertion opening, both in communication with the lumen, and also a distal side hole in communication with the lumen. The distal side hole is closer to the distal end of the tubular member than the proximal end thereof. The sheath includes means for peelably removing at least a portion of the tubular member from a guide member extending through the lumen. Said means permits separation of said portion of the tubular member from the guide member outside the patient as the tubular member is proximally withdrawn from the patient's vasculature while the guide member remains generally stationary.

In operation, the sheath is initially inserted into a patient for use along a pre-inserted guide member by inserting a proximal end of the guide member into the distal insertion opening of the tubular member and advancing the tubular member distally over the preinserted guide member. The proximal end of the preinserted guide member thus runs through the lumen of the tubular member until it reaches the distal side hole where it exits the lumen. The sheath is then further advanced distally into the patient until its distal end is positioned adjacent the distal end of the preinserted guide member. In one preferred embodiment, a longitudinal stiffening member is placed in the lumen of the tubular member to extend proximally from the distal side hole thereof to aid in reinforcing the sheath for distal advancement. The guide member is then withdrawn proximally from the patient's vasculature while the sheath is held generally stationary (the stiffening member is also proximally withdrawn, if applicable). A distal end of a second guide member (either the first one reshaped or an alternative guide member) is then inserted into the exposed proximal insertion opening of the tubular member and advanced distally through the lumen of the tubular member to a desired position in the patient. After a reshaped or substitute guide member is advanced to a desired position, the sheath is removed by withdrawing it proximally and peelably removing the tubular member from the guide member outside the patient.

In the above-described operational summary, the sheath is used for exchanging one guide member for another. If a single operator exchange intravascular device had already been placed on the pre-inserted guide member, it must first be proximally removed over the guide wire before the sheath exchange procedure outlined above is performed. After a second guide member is then in place, as desired, the same or another single operator exchange intravascular device may be placed on the second guide member and advanced distally to a desired position in the patient's vasculature. In one preferred embodiment of the sheath, removal of the single operator exchange intravascular device is not necessary to accomplish guide member exchange. In this embodiment the sheath includes means for aligning its distal insertion opening with a proximal opening in the guide member lumen of the single operator exchange intravascular device while the device remains within the patient's vasculature. In this instance, the sheath is advanced over the pre-inserted guide member until so aligned, the guide member withdrawn proximally through the device and sheath and a second guide member inserted from a proximal end of the sheath to its distal end where, because of the alignment between the distal insertion opening of the tubular member and the proximal opening of the guide member lumen of the device, the distal end of the guide member exits the sheath and enters the proximal opening of the guide member lumen in the device. Except as mentioned above, use of the sheath in the various situations is otherwise operationally the same.

In one preferred embodiment of the sheath, the means for peelably removing the tubular member from the guide member is a slit through the elongated tubular member extending distally from the proximal insertion opening. Alternatively, the means for peelably removing may be formed of a longitudinally extending area of reduced wall thickness of the elongated tubular member extending distally from the proximal insertion opening. The area of reduced wall thickness may be easily torn for removing the sheath. Alternatively, the means for peelably removing may be defined by a perforated extent including a series of alternating cut segments and connecting segments extending distally along the tubular member from the proximal insertion opening. As another alternative, the tubular member may be formed of a tearable material for removing the sheath from the guide wire.

BRIEF DESCRIPTION OF THE DRAWINGS

The invention will be further described with reference to the accompanying drawings where like numbers refer to like parts in several views and wherein:

FIG. 1 is a perspective view of a first embodiment of the sheath of the present invention.

FIG. 2 is a top elevational view of the sheath as shown in FIG. 1.

FIG. 6 is an illustrative view of a "single-operator exchange" type catheter shown inserted through a guide catheter of a typical patient for placement at a treatment site.

FIG. 9a is a perspective view of a second embodiment of the sheath of the invention having a tearable extent where the tearable extent is formed of a shaved longitudinal section.

FIG. 9b is a perspective view of a second embodiment of the sheath of the invention having a tearable extent where the tearable extent is formed by a heating process.

FIG. 10a is a cross-sectional view taken along line 10a—10a of FIG. 9a.

FIG. 10b is a cross-sectional view taken along line 10b—10b of FIG. 9b.

FIG. 11 is a cross-sectional view taken along line 11—11 of FIG. 9a.

FIG. 12 is a perspective view of a third embodiment of the sheath of the invention.

FIG. 13 is a top elevational view of a third embodiment of the sheath of the invention.

FIG. 17 is a side elevational view illustrating use of the sheath of FIG. 15 with a "single operator exchange" type catheter device.

Figure 3:
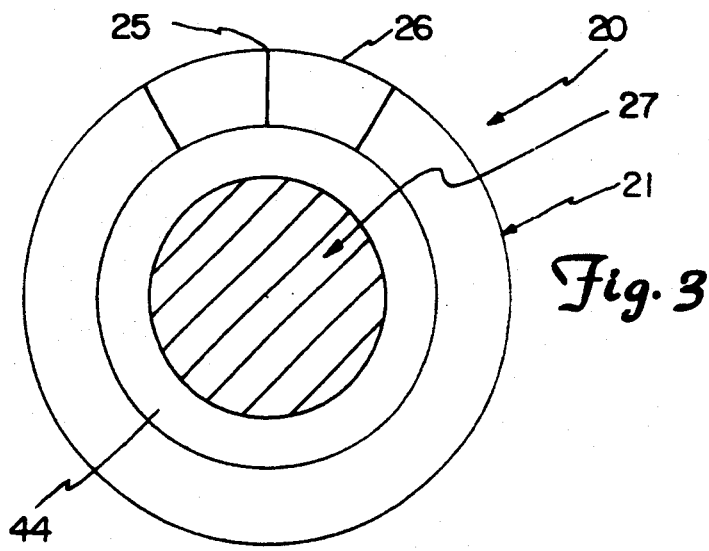
FIG. 3 is a cross-sectional view taken along line 3—3 of FIG. 1.
Figure 4:
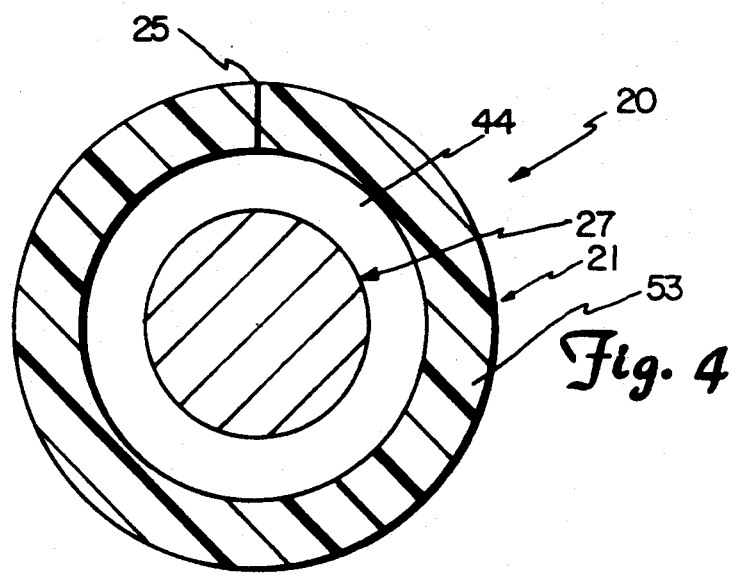
FIG. 4 is a cross-sectional view taken along line 4—4 of FIG. 1.
Figure 5:
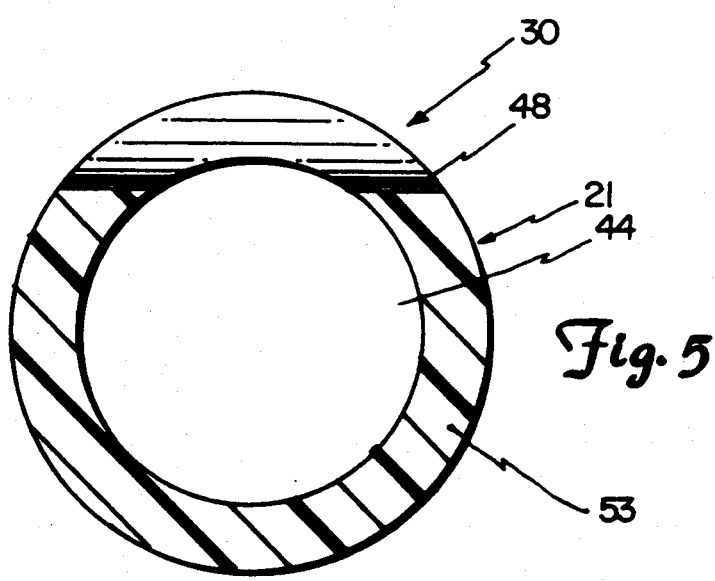
FIG. 5 is a cross-sectional view taken along line 5—5 of FIG. 1.

While the above identified drawing figures set forth several preferred embodiments, other embodiments of the present invention are also contemplated, as noted in the discussion. In all cases, this disclosure presents illustrated embodiments of the present invention by way of representation and not limitation. It should be understood that numerous other modifications and embodiments can be devised by those skilled in the art which fall within the scope and spirit of the principles of this invention. It should be noted that the figures have not been drawn to scale as it has been necessary to enlarge certain portions for clarity.

DETAILED DESCRIPTION OF THE PREFERRED EMBODIMENTS

Introduction

The sheath of the present invention is intended for use with a "single operator exchange" intravascular device and in particular a "single operator exchange" angioplasty catheter device. A "single operator exchange" angioplasty catheter device includes a guide wire lumen which extends only along a distal portion of the catheter. The sheath of the present invention provides for simplified guide wire exchanges for a "single operator exchange" angioplasty catheter device.

The sheath may also be used to exchange a guide wire which is inserted alone and does not extend through a guide wire lumen of a "single operator exchange" type therapeutic or diagnostic device to maintain the position of the guide wire so that after the guide wire is withdrawn, a physician does not need to retrace a path through the patient to re-insert a guide wire.

Several embodiments of the sheath are disclosed, however, it should be understood that the invention is not intended to be limited to those embodiments shown. Other embodiments are also contemplated and are within the scope of the invention. Furthermore, although use of the device is explained with reference to treating coronary arteries it should be understood that the device may also be used in connection with therapeutic or diagnostic treatment of other diseased vessels in a patient or in connection with other therapeutic or diagnostic procedures which utilize a guide wire as well.

Description of the First Embodiment of the Sheath of the Invention (FIGS 1-5)

FIGS. 1-5 illustrate a first embodiment of the sheath 20 of the invention. The sheath 20 includes an elongated tubular member 21, proximal insertion opening 22, distal insertion opening 23, a distal guide segment 24, longitudinal slit 25, peeling notch 26 and stiffening member 27. The distal guide segment 24 includes a guide lumen 28, a distal thread opening 29 and a proximal thread opening 30. As shown in FIGS. 1 and 2, radiopaque markers 32 and 33 are included to trace the position of the guide catheter sheath 20 during operation.

The elongated tubular member 21 has a proximal end 34 and a distal end 35 and includes a proximal opening 36, a distal opening 38, a first diameter segment 40, a second diameter segment 42, a single thru lumen 44 and a transition portion 46. The proximal opening 36 of the tubular member 21 defines the proximal insertion opening 22 in communication with the thru lumen 44 which remains outside the patient when the sheath 20 is advanced for use. The distal opening 38 defines the distal insertion opening 22 in communication with the thru lumen 44.

The distal guide segment 24 provides for "single operator" insertion of the sheath 20 and is defined by a distal extent of the tubular member 21 so that thru lumen 44 of the tubular member along segment 24 is also the guide lumen 28 for "single operator" insertion of the sheath 20 along a pre-inserted guide wire. The distal opening 38 defines the distal thread opening 29 of the distal guide segment 24. A side hole 48 through a side wall of the tubular member is proximally spaced from the distal thread opening 29 to define proximal thread opening 30 of the distal guide segment 24.

The distal opening 38 and the side hole 48 are spaced to provide a relatively short distal guide segment 24 which extends only along a distal portion of the sheath 20. A pre-inserted guide wire extends through guide lumen 28 (and distal thread opening 29 and proximal thread opening 30) of the distal guide segment 24 for tracking the sheath 20 along the guide wire for insertion of the sheath 20.

The extent of the distal guide segment 24 of the sheath 20 is sized so that when a standard sized guide wire (approximately 175 cm in length) extends through the guide lumen 28 of the distal guide segment 24 for insertion of the sheath 20, a portion of the guide wire (outside the patient) extends outside the distal guide segment 24 of the sheath 20. The exposed portion of the guide wire outside the distal guide segment 24 may be gripped for manipulation of the guide wire. Since a portion of the guide wire outside the patient extends outside the distal guide segment 24, a guide wire extension is not necessary since the operator may directly grip an exposed portion of the guide wire at all times for control of the guide wire. Accordingly, the distal guide segment 24 defines means for "single operator" insertion so that a guide wire extension is not necessary.

An outer diameter of the second diameter segment 42 of the tubular member 21 is smaller than the outer diameter of the first diameter segment 40. The transition portion 46 is distally tapered and is between the first diameter segment 40 and the second diameter segment 42. The first diameter segment 40 extends from proximal end 34 to the transition portion 46 of the tubular member 21. The second diameter segment 42 extends from the transition portion 46 to the distal end 35 of the tubular member 21. The transition portion 46 provides a gradual transition between the first diameter segment 40 and the second diameter segment 42. The thru lumen 44 is sized to receive a guide wire therethrough. Preferably, the thru lumen 44 is sized to receive a single guide wire therethrough.

The peeling notch 26 is formed at the proximal end 34 of the tubular member 21. The notch 26 includes a mouth 50 and a tip portion 52. The slit 25 is formed through a side wall 53 of the tubular member 21 and extends from the tip portion 52 of notch 26 preferably to the side hole 48 (See FIG. 2).

Marker 32 is formed of a cylindrical coil or band of radiopaque material and is mounted about the first diameter portion 40 adjacent to the side hole 48. Marker 33 is also formed of a cylindrical coil or band of radiopaque material and is mounted about the second diameter portion 42 at the transition portion 46. An adhesive fill 54 is used to provide a smooth transition between the outer diameter of the radiopaque marker 33 and the outer diameter of the second diameter portion 42 to eliminate an abrupt change in diameter. Preferably the adhesive fill 54 is an epoxy.

The stiffening member 27 is formed of a relatively stiff elongated cylindrical rod and is preferably designed for slidable insertion into the thru lumen 44 (at the proximal opening 36) of the elongated tubular member 21. The stiffening member 27 is long enough so that a portion of the stiffening member 27 extends outside the tubular member 21 some distance and extends through the thru lumen 44 of the tubular member 21 preferably to the distal side hole 48. The stiffening member 27 includes a series of distally decreasing diameter segments, preferably, a first member segment 27a, a second member segment 27b, and a third member segment 27c. The first member segment 27a has the largest outer diameter and the second and third member segments 27b and 27c have successively smaller outer diameters.

Preferably, the elongated tubular member 21 is 53.2 inches (135 cm) in length. The first diameter segment 40 of the tubular member 21 is formed from a polyethylene tube having an inner diameter dimension of 0.021 to 0.025 inches (0.53 to 0.635 mm) and an outer diameter in the range of 0.028 to 0.034 inches (0.711 to 0.864 mm). Preferably, the inner diameter dimension is 0.021 inches (0.53 mm) and the outer diameter dimension is 0.028 inches (0.711 mm). The tubular member 21 may be formed of other polymer materials such as polyolefin copolymer. The tubular member 21 is preferably coated with a silicone type coating or hydrophilic coating to provide a more lubricous surface.

The second diameter segment 42 is formed at a distal portion of the polyethylene tube by a necking down process where the tube is drawn through a heated die. A mandrel (not shown) is used to maintain a constant inner diameter of preferably 0.021 (0.53 mm) along the necked down second diameter segment 42. The second diameter segment 42 is preferably necked down to a 0.025 inch (0.635 mm) outer diameter. The first diameter segment 40 is 53.0 inches long (134.5 cm) and the second diameter segment 42 is 0.2 inches long (5 mm) to support the radiopaque marker 33.

The distal side hole 48 is located 1.97 to 3.94 inches (5 to 10 cm) from the distal end 35 of the tubular member 21. The distal side hole 48 is formed by a skiving process where a mandrel (not shown) is inserted into the thru lumen 44 at the location of the side hole 48. A razor blade is used to cut the tubular member 21 to form the side hole 48. The depth of the cut is controlled by the mandrel (not shown). Preferably, the diameter of the mandrel is 0.018 inches (0.46 mm). Thus when the blade hits the mandrel, (not shown) the direction of the cut shifts to form the length of the distal side hole 48. The length of the distal side hole 48 is sufficient to allow a guide wire to extend therethrough for use, preferably 0.40 to 0.79 inches (10 to 20 mm). Alternatively, the side hold 48 is formed of a geometry such that when a guide wire is advanced distally through the lumen 28 from the proximal insertion opening 22, the guide wire will not readily exit the lumen via the side hole 48, but rather continue distally through the lumen 28 toward the distal insertion opening 23.

The notch 26 is cut at the proximal end 34 of the tubular member 21 using a razor blade or other cutting method. The extent of the notch 26 between the mouth 50 and the tip 52 is 0.125 to 0.25 inches (3.175 to 6.35 mm). The width of the mouth 50 is preferably approximately 0.021 inches (0.53 mm). The notch is formed to provide a "peeling handle" or starting point for the separation of the tubular member 21 and guide wire to occur.

The stiffening member 27 is formed of stainless steel material. The length of the member 27 is approximately 55.16 inches (140 cm). In use, a portion of the stiffening member 27 always extends proximally out of the proximal opening 36 of the tubular member 21 some distance for control of the stiffening member 27. The first member segment 27a is 0.014 inches in diameter (0.355 mm). The second member segment 27b is 0.009 inches in diameter (0.23 mm). The third member segment 27c is 0.006 inches in diameter (0.15 mm). The length of the first member segment 27a is 44.66 inches (113.35 cm). The length of the second member segment 27b is 8.0 inches (20.3 cm). The length of the third member segment 27c is 2.5 inches (6.35 cm). The distally decreasing diameter segments of the stiffening member 27 provide flexibility to allow the sheath 20 (and stiffening member 27) to negotiate the vascular system of the patient.

Preferably the stiffening member 27 is coated with a Teflon® coating. Teflon® is a registered trademark of E. I. du Pont de Nemours & Co., Inc. of Delaware for polytetrafluorethylene. The Teflon® coating slightly increases the outer diameters of the successive member segments 27a, 27b and 27c (e.g., by 0.0004 inches, 0.01 mm). Alternatively, the stiffening member 27 may also be coated with another lubricous material such as a hydrophilic polymer coating or silicone coating to provide a more lubricous surface.

Although a discrete stiffening member 27 is illustrated, it is contemplated that other means for stiffening the tubular member 21 of the sheath are contemplated. For adequate advancement characteristics, it is necessary for the tubular member 21 to have sufficient pushability proximally of the side hole 48. As illustrated, this may attained by a stiffening member 27 received within the lumen 28. Alternatively, the proximal portion of the tubular member may be formed of a material of sufficient rigidity or stiffness that no discrete stiffening member is necessary. Further, the tubular member 21 may include embedded stiffening members (such as longitudinal embedded stiffeners) or may be otherwise enhanced in pushability characteristics by additional reinforcement such as braiding.

Figure 6A:
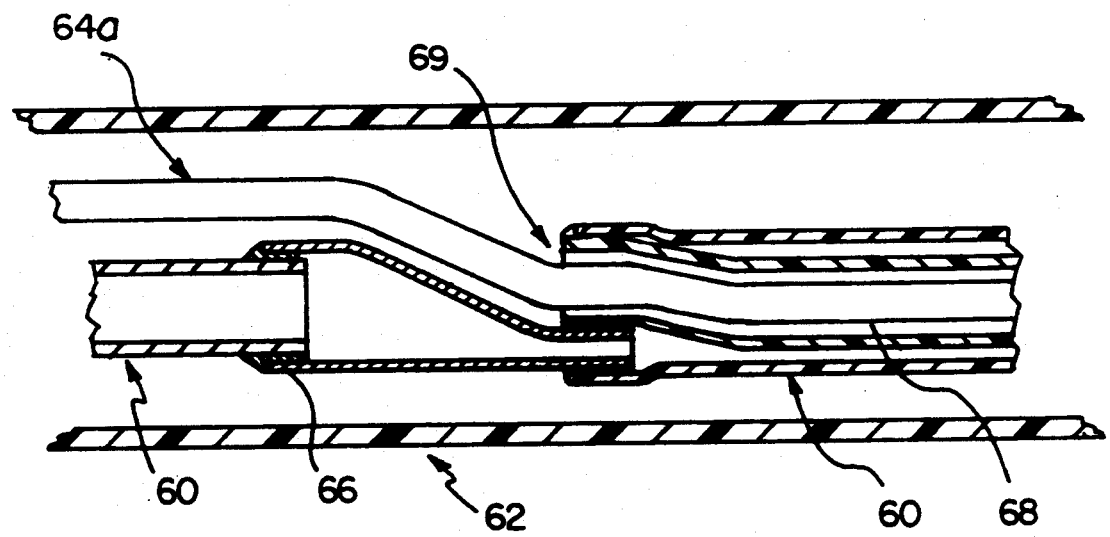
FIG. 6a is a enlarged detailed view, in crosssection, of a portion of the "single operator exchange" type catheter as shown in FIG. 6 as indicated.
Figure 7:
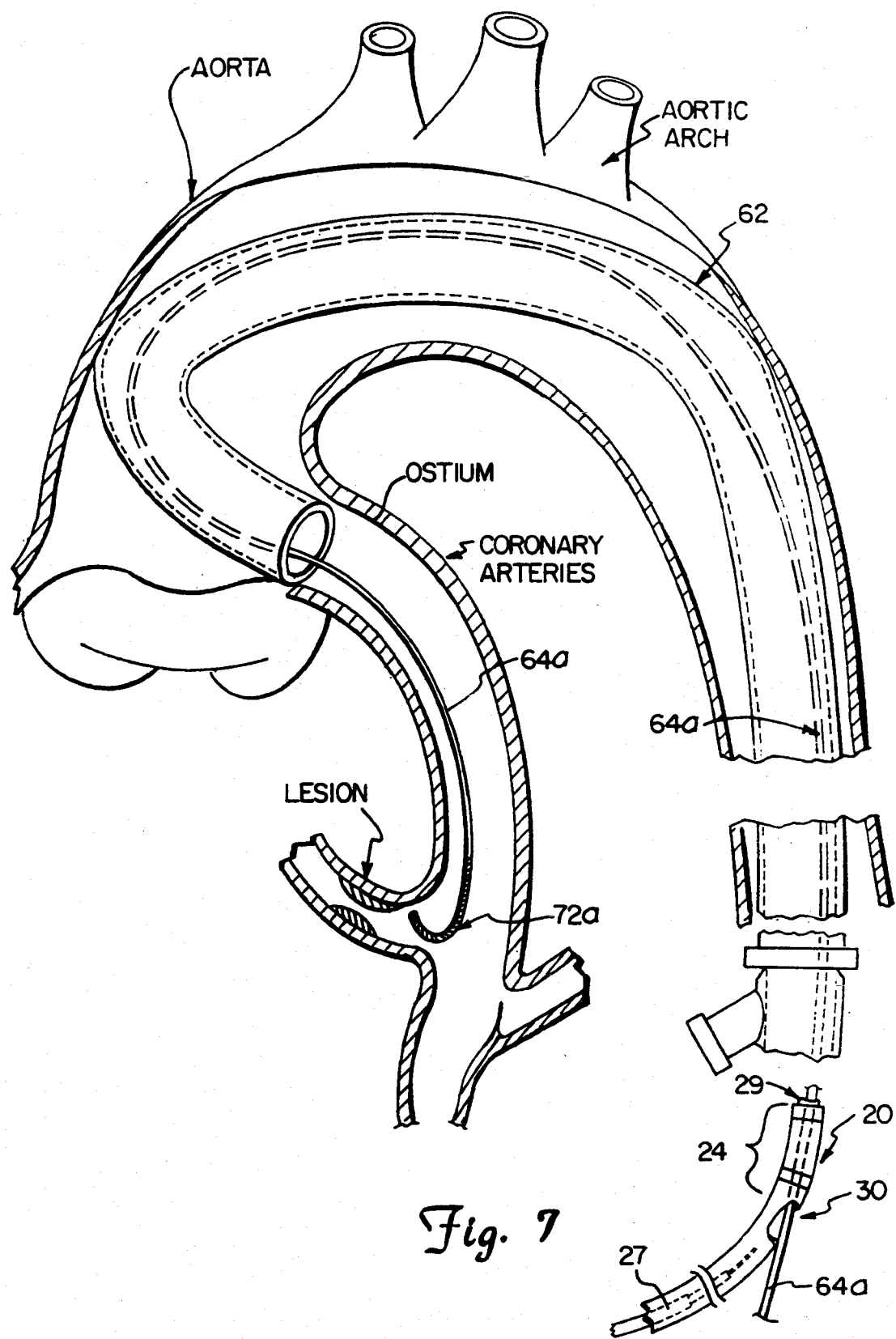
FIG. 7 is an illustrative view of the sheath being inserted along a pre-inserted guide wire after the "single operator exchange" type catheter has been withdrawn from the patient.
Figure 8:
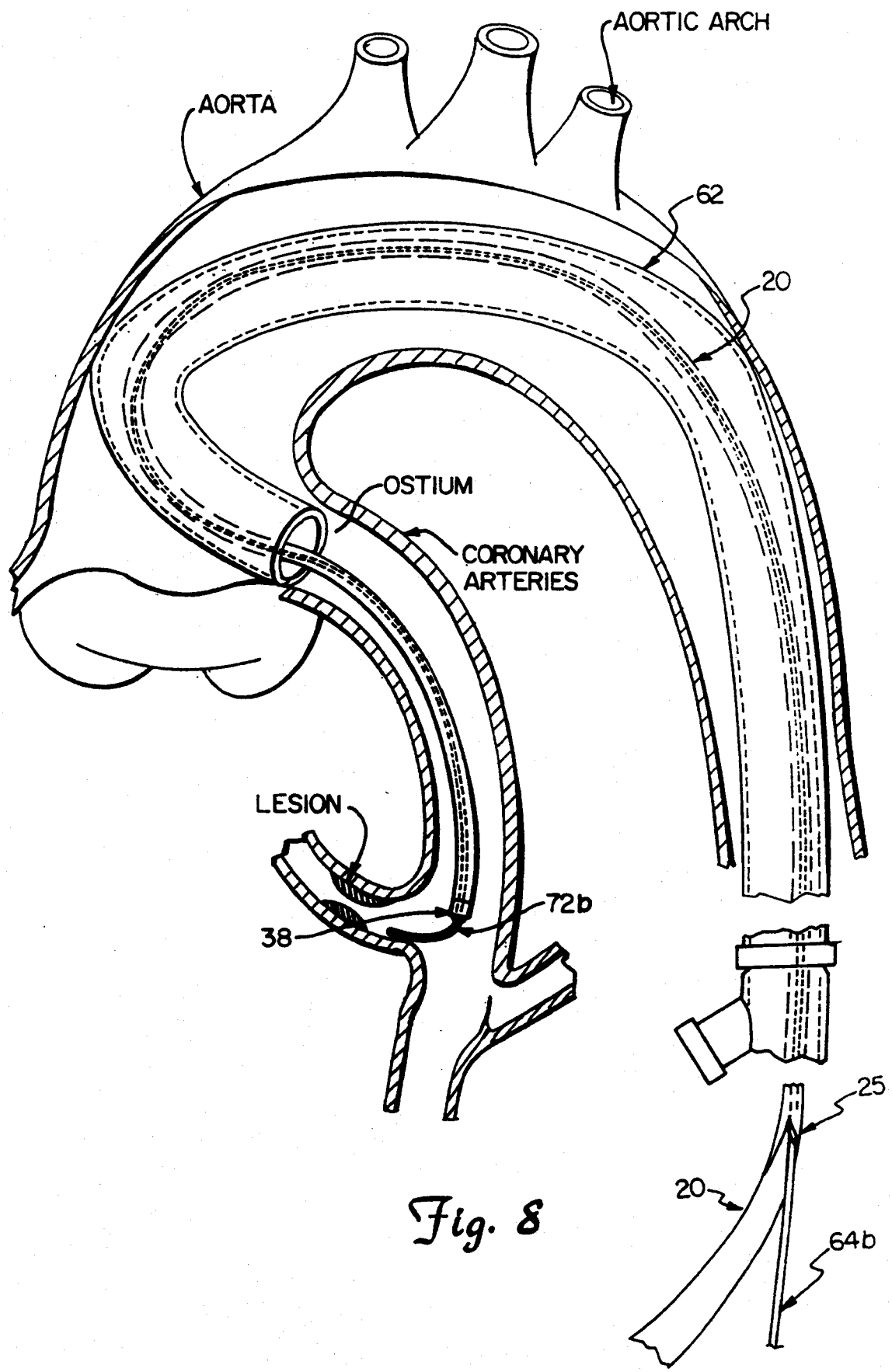
FIG. 8 is an illustrative view showing a guide wire which has been advanced and positioned via the sheath, and showing a proximal portion of the sheath being peeled away from the guide wire.

Description of Operation of the Sheath of the Invention (FIGS. 6–8)

FIGS. 6–8 illustrate a coronary artery having a lesion or blockage which requires treatment. Coronary arteries extend from the aorta and provide blood to nourish the heart muscle. To provide treatment to the lesion or blocked area of a coronary artery, an intravascular device is typically advanced from the femoral artery (not shown) of a patient through the aorta and further into the coronary artery to treat a lesion.

Coronary angioplasty has proven particularly successful for treating blocked or diseased coronary arteries. Coronary angioplasty makes use of a balloon catheter device to stretch the blocked artery or compress plaque which has deposited in the artery to reestablish an acceptable blood flow through the artery.

FIGS. 6 and 6a illustrates a balloon catheter 60 inserted into a patient for performing coronary angioplasty. The balloon catheter 60 shown is a "single operator exchange" type catheter. A guide catheter 62 is inserted to guide the "single operator exchange" balloon catheter 60 to the ostium of the coronary artery. The "single operator exchange" balloon catheter 60 is advanced in combination with a guide wire 64a through the guide catheter 62 and through the coronary artery to the treatment site.

The "single operator exchange" balloon catheter 60 includes a catheter shaft 66, a distal guide wire lumen 68, proximal guide wire lumen opening 69 and balloon 70. The distal guide wire lumen 68 extends only along a distal portion of the catheter shaft 66 and has a distal tip 72a. The distal tip 72a is formed of a flexible construction that includes a forming ribbon which allows the distal tip 72a to be bent to a desired shape, in anticipation of the need for negotiating the curvature of the coronary artery requiring treatment. The guide wire 64a extends through the proximal guide wire lumen opening 69 into the guide wire lumen 68 of the balloon catheter 60 to advance and direct the balloon catheter 60 to the coronary artery requiring treatment.

Often times, the distal tip 72a of the guide wire 64a has not been correctly shaped in the first instance to permit the guide wire 64a to be steered and advanced into the coronary artery requiring treatment. In particular, as illustrated by FIG. 6, further advancement of the guide wire 64a will fail to properly direct the distal tip 72a into the coronary artery with the lesion. Alternatively, the distal tip 72a may have been properly shaped in the first instance but now must be reshaped or an alternate guide wire may be necessary to reach and treat a second lesion.

In either event, it is necessary to perform a guide wire exchange (either withdraw the guide wire 64a from the patient to reshape the distal tip 72a or substitute another guide wire). Once the guide wire 64a is withdrawn, it is extremely difficult, if not impossible to re-insert a reshaped or substitute guide wire through the proximal guide wire lumen opening 69 into the guide wire lumen 68 since the proximal guide wire lumen opening 69 is inside the patient and not visible or accessible to the operator. The sheath 20 of the present invention addresses this situation by providing a conduit for inserting a reshaped or substitute guide wire into the patient for use advancing and directing a "single operator exchange" balloon catheter to a treatment site.

As shown in FIG. 7, to perform a guide wire exchange, the "single operator exchange" balloon catheter 60 is proximally withdrawn from the patient and guide wire 64a. The distal guide segment 24 of the sheath 20 is mounted about the proximal end of the guide wire 64a for "single operator" insertion so that the guide wire 64a extends through the guide lumen 28, from the distal thread opening 29 to the proximal thread opening 30. As shown in FIG. 7, the extent of the distal guide segment 24 is sized so that when the distal guide segment 24 is mounted about the proximal end of the guide wire 64a, a portion of the guide wire 64a outside the patient (and guide catheter 62) extends outside of the distal guide segment 24 of the sheath 20 so that the guide wire 64a may be gripped to control the guide wire 64a and insert the sheath 20 without a guide wire extension for "single operator" insertion.

The distal guide segment 24 of the tubular member 21 is then distally advanced along the guide wire 64a to insert the sheath 20 into the guide catheter 62 and the patient. During this original advancement onto the guide wire 64a, the stiffening member 27 is within the lumen 28 of the tubular member 21 and its distal end is at or proximal to the side hole 48. The sheath 20 is advanced until the distal end 35 of the sheath 20 is placed in a desired alignment with the distal tip 72a of the guide wire 64a. After the sheath 20 is so aligned, the guide wire 64a and stiffening member 27 are proximally withdrawn from the patient while maintaining the guide wire exchange sheath 10 generally stationary in the patient's vasculature.

Once the guide wire 64a is fully withdrawn, the tip 72a may be reshaped as shown in FIG. 8 so that the tip configuration is better adapted to steer into the coronary artery requiring treatment or a new substitute guide wire may be inserted. The guide wire 64b (the original guide wire 64a with a reshaped distal tip 72b or a substitute guide wire) is inserted through the proximal insertion opening 22 of the sheath 20 and advanced distally through the thru lumen 44 of the tubular member 21 to the treatment site. The guide wire 64b is then advanced until the distal tip 72b extends through the distal insertion opening 23 of the tubular member 21. The guide wire 64b is then further steered to advance its distal tip 72b across the stenosis in the artery.

Thereafter, as shown in FIG. 8, the sheath 20 is removed from the patient by withdrawing the sheath 20 proximally and peeling the tubular member 21 from about the guide wire 64b along the slit 25 (while the guide wire 64b is held stationary relative to the stenosis). The peeling notch 26 (not shown in FIG. 8) facilitates initiation of the peeling of the sheath 20 from the guide wire 64b. Since, as preferred, the slit 25 extends only to the distal side hole, the tubular member 21 is withdrawn while peelably removing the tubular member 21 until the distal side hole 48 is withdrawn from the patient. Thereafter, the remaining portion of the sheath 20 (i.e., the distal guide segment 24) is slid proximally off the proximal end of the guide wire. After the sheath 20 is removed, the "single operator exchange" balloon catheter is reinserted along the guide wire 64b to dilate the lesion.

Description of the Second Embodiment of the Sheath of the Invention (FIGS. 9–11)

FIGS. 9–11 disclose a second embodiment of the sheath 100 of the invention. The sheath 100 includes an elongated tubular member 102, proximal insertion opening 103, distal insertion opening 104, distal guide segment 105, a tearable extent 106, tear tab 107, and a stiffening member 108. The distal guide segment 105 includes a guide lumen 109, a distal thread opening 110 and a proximal thread opening 111. As shown in FIGS. 9a & 9b, radiopaque markers 112 and 114 are included to trace the position of the sheath 100 during operation. Marker 115 is included to locate the proximal insertion opening 103.

The elongated tubular member 102 has a proximal end 116 and a distal end 118 and includes a proximal opening 120, a proximal side hole 121, a distal opening 122, a first diameter segment 124, a second diameter segment 126, a single thru lumen 128 and a transition portion 130. The proximal side hole 121 through a side wall of the tubular member 102 defines the proximal insertion opening 103 which remains outside the patient when the sheath 100 is advanced for use. The distal opening 122 of the tubular member 102 defines the distal insertion opening 104 of the sheath 100 in communication with the thru lumen 128.

The distal guide segment 105 provides for "single operator" insertion of the sheath 100 and is defined by a distal extent of the tubular member 102 so that thru lumen 128 of the tubular member 102 along segment 105 is also the guide lumen 109 for "single operator insertion" of the sheath 100 along a preinserted guide wire. The distal opening 122 defines the distal thread opening 110 of the distal guide segment 105. A side hole 132 through the side wall 131 of the tubular member 102 is proximally spaced from the distal thread opening 110 to define the proximal thread opening 111 of the distal guide segment 105.

The distal opening 122 and the side hole 132 are spaced to provide a relatively short distal guide segment 105 which extends only along a distal portion of the sheath 100. A pre-inserted guide wire extends through the guide lumen 109 (and distal thread opening 110 and proximal thread opening 111) of the distal guide segment 105 for tracking the sheath 100 along the guide wire for insertion. Since the distal guide segment 105 extends only along a relatively short distal segment of the sheath 100, the distal guide segment 105 defines means for "single operator" insertion so that a guide wire extension is not necessary.

An outer diameter of the second diameter segment 126 is smaller than the outer diameter of the first diameter segment 124. The transition portion 130 is distally tapered and is between the first diameter segment 124 and the second diameter segment 126. The first diameter segment 124 extends from the proximal end 116 to the transition portion 130 of the tubular member 102. The second diameter segment extends from the transition portion 130 to the distal end 118 of the tubular member 102. The transition portion 130 provides a gradual transition between the first diameter segment 124 and the second diameter segment 126. The thru lumen 128 is sized to receive a guide wire therethrough. Preferably the thru lumen 128 is sized to receive a single guide wire therethrough.

Marker 115 is an ink mark, preferably made by a Sharpie® fine point permanent marker. Sharpie® is a registered trademark of Sanford Corporation of Illinois. The ink marker 115 extends about the outer circumference of the first diameter segment 124 at the proximal side hole 121 to provide a quickly perceivable visible locator for the proximal insertion opening 103.

As shown FIGS. 9a and 10a, the tearable extent 106 is preferably defined by a shaved longitudinal section 136 of the elongated tubular member 102. The shaved longitudinal section 136 defines an area of reduced wall thickness for peeling the sheath 100 from a guide wire which has been inserted into thru lumen 128. The shaved longitudinal section 136 may be formed using a cutting fixture or by grinding the tubular member 102.

The shaved longitudinal section 136 extends distally from the proximal side hole 121 (proximal insertion opening 103) preferably to the distal side hole 132 to provide a means for peelably removing the sheath 100 after use. Preferably, as shown FIG. 9a, the shaved longitudinal section 136 extends proximally beyond the proximal side hole 121 (proximal insertion opening 103) to the proximal end 116 of the tubular member 102.

Alternatively, as shown in FIGS. 9b and 10b, the tearable extent 106 may be formed by weakening a longitudinal extent of the tubular member 102 by a heating process to form an area of reduced wall thickness 137 (FIG. 10b). To weaken a longitudinal extent of the tubular member 102, a conductive mandrel is inserted into the thru lumen 128 adjacent the side wall 131 of the tubular member 102. Current is passed through the mandrel to melt the wall 131 of the tubular member 102 to form the tearable extent 106.

As another alternative, the tubular member 102 may be formed of an irradiated polyolefin copolymer material or other such material which may be easily torn by an operator for removal of the sheath 100 after use. An acceptable material to use for the tubular member 102 would require a removal force of no more than approximately 0.155 kg force.

Marker 112 is formed of a cylindrical coil or band of radiopaque material and is mounted about the first diameter portion 124 adjacent to the distal side hole 132. Marker 114 is also formed of a cylindrical coil or band of radiopaque material and is mounted about the second diameter portion 126 at the transition portion 130. An adhesive fill 140 is used to provide a smooth transition between the outer diameter of the radiopaque marker 114 and the outer diameter of the second diameter portion 126 to eliminate an abrupt change in diameter. Preferably the adhesive fill 140 is an epoxy.

The stiffening member 108 is formed of a relatively stiff elongated cylindrical rod and is preferably designed for slidable insertion into the thru lumen 128 (at the proximal opening 120) of the elongated tubular member 102. The stiffening member 108 is long enough so that a portion of the stiffening member 108 extends outside the tubular member 102 some distance and extends through the thru lumen 128 of the tubular member 102 preferably to the distal side hole 132. The stiffening member 108 includes a series of distally decreasing diameter segments, preferably, a first member segment 108a, a second member segment 108b, and a third member segment 108c. The first member segment 108a has the largest outer diameter and the second and third member segments 108b and 108c have successively smaller outer diameters. Preferably, the elongated tubular member 102 is 53.2 inches (135 cm) in length. The first diameter segment 124 is formed from a polyethylene material tube having an inner diameter dimension of 0.021 to 0.025 inches (0.53 to 0.635 mm) and an outer diameter in the range of 0.028 to 0.034 inches (0.711 to 0.864 mm). Preferably, the inner diameter dimension is 0.021 inches (0.53 mm) and the outer diameter dimension is 0.028 inches (0.711 mm) so the normal wall thickness of the tubular member 102 is 0.0035 inches (0.089 mm). The outer diameter at shaved longitudinal section 136 is reduced to 0.025 inches (0.635 mm) to define a 0.002 inches (0.05 mm) wall thickness. The tubular member 102 may be formed of other polymer materials such as polyolefin copolymer. The tubular member 102 is preferably coated with a silicone type coating or hydrophilic coating.

The second diameter segment 126 is formed at a distal portion of the polyethylene tube by a necking down process where the tube is drawn through a heated die. A mandrel (not shown) is used to maintain a constant inner diameter of preferably 0.021 (0.53 mm) along the necked down second diameter segment 126. The second diameter segment 126 is preferably necked down to a 0.025 inch (0.635 mm) outer diameter. The first diameter segment 124 is 53.0 inches long (134.5 cm) and the second diameter segment 126 is 0.2 inches long (5 mm) to support the radiopaque marker 114.

The distal side hole 132 is located 1.97 to 3.94 inches (5 to 10 cm) from the distal end 118 of the tubular member 102. The distal side hole 132 is formed by a skiving process as previously described in relation to the sheath 20 of the first embodiment and is similarly dimensioned.

The proximal side hole 121 is located 1.0 to 2.0 inches (25.4 to 50.8 mm) from the proximal end 116 of the tubular member 102 so that the proximal side hole 121 remains outside the patient while the sheath 100 is inserted for use. Thus, the proximal insertion opening 103 is accessible to the operator to insert a guide wire therethrough. The proximal side hole 121 is similarly formed as the distal side hole 132 as described above. The proximal side hole 121 is dimensioned similar to the distal side hole 132. The extent between the proximal side hole 121 and the proximal end 116 of the tubular member 102 defines the tab 107 which facilitates the removal of the sheath 100 from a guide wire after use.

The stiffening member 108 is formed of stainless steel material. The length of the stiffening member 108 is approximately 55.16 inches (140 cm). In use, a portion of the stiffening member 108 always extends proximally out of the proximal opening 120 of the tubular member 102 some distance for control of the stiffening member 108. The first member segment 108a is 0.014 inches in diameter (0.355 mm). The second member segment 108b is 0.009 inches in diameter (0.23 mm). The third member segment 108c is 0.006 inches in diameter (0.15 mm). The length of the first member segment 108a is 44.66 inches (113.35 cm). The length of the second member segment 108b is 8.0 inches (20.3 cm). The length of the third member segment 108c is 2.5 inches (6.35 cm). The distally decreasing diameter segments of the stiffening member 108 provide flexibility to allow the sheath 100 (and stiffening member 108) to negotiate the vascular system of the patient.

Preferably the stiffening member 108 is coated with a Teflon® to provide a lubricous surface. The coating slightly increases the outer diameters of the successive member segments 108a, 108b and 108c. (e.g., by 0.0004 inches, 0.01 mm). Alternatively, the stiffening member 108 may also be coated with another lubricous material such as a hydrophilic polymer coating or silicone coating to provide a more lubricous surface.

The operation of the sheath 100 of FIG. 9–11 is similar to that described in relation to FIGS. 6–8 for the first embodiment of the sheath 20. To facilitate an exchange, the proximal end of a preinserted guide wire is inserted into the guide lumen 109 of the distal guide segment 105 through the distal thread opening 110 and the proximal thread opening 111. Thereafter, the sheath 100 is advanced (with the stiffening member 108) distally along the pre-inserted guide wire for "single operator insertion" to place the distal end 118 of the tubular member 102 in a desired alignment with the distal tip of the guide wire. After the sheath 100 is inserted, the pre-inserted guide wire and stiffening member 108 are withdrawn proximally from the sheath 100 and removed from the patient. After the pre-inserted guide wire and stiffening member 108 are removed, the distal tip of the removed guide wire may be re-shaped or a substitute guide wire may be inserted for operation via the thru lumen 128 of the sheath 100.

The substitute or reshaped guide wire is inserted into the thru lumen 128 via the proximal insertion opening 103. The substitute or re-shaped guide wire is then advanced distally to the distal end 118 of the elongated tubular member 102. Thereafter, the sheath 100 is withdrawn proximally from the patient and removed from the guide wire by pulling laterally on the tab 107 (relative to the guide wire) to initiate the tearing of the reduced wall section 137 of the sheath 100. The tab 107 is further pulled in this manner to tearably remove the proximal portion of the elongated tubular member 102 (up to the distal side hole 132) from the guide wire.

When the proximal thread opening 111 is withdrawn from the patient, the remaining portion of the sheath (i.e., the distal guide segment 105) is slid proximally off the proximal end of the guide wire. The length of the distal guide segment 105 is small enough so that the user or operator may withdraw the sheath 100 while maintaining control of the guide wire so that longitudinal movement of the guide wire relative to the patient's vasculature is minimized.

Figure 14:
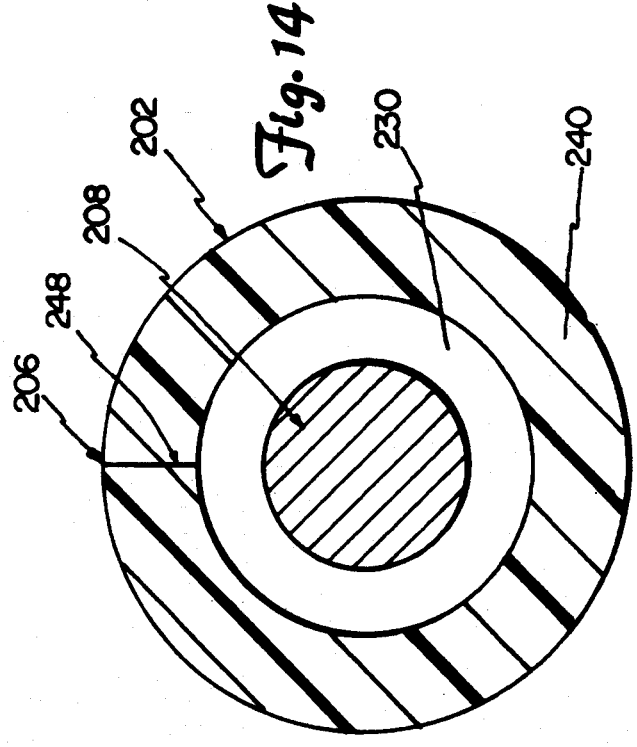
FIG. 14 is a cross-sectional view taken along line 14—14 of FIG. 13.

Description of the Third Embodiment of the Sheath of the Invention (FIGS. 12–14)

FIGS. 12–14 illustrate a third embodiment of the sheath 200 of the invention. The sheath 200 includes an elongated tubular member 202, proximal insertion opening 203, distal insertion opening 204, distal guide segment 205, perforated extent 206, peeling notch 207 and stiffening member 208. The distal guide segment 205 includes a guide lumen 209, a distal thread opening 210 and a proximal thread opening 211. As shown FIGS. 1 and 2, radiopaque markers 212 and 214 are included to trace the position of the guide catheter sheath 200 during operation.

The elongated tubular member 202 has a proximal end 216 and a distal end 218 and includes a proximal opening 220, a distal opening 222, a flared section 224, a first diameter segment 226, a second diameter segment 228, a single thru lumen 230 and a transition portion 232. The proximal opening 220 of the tubular member 202 defines the proximal insertion opening 203 in communication with the thru lumen 230 which remains outside the patient when the sheath 200 is advanced for use. The distal opening 222 of the tubular member 202 defines the distal insertion opening 204 in communication with the thru lumen 230 of the sheath 200.

The flared section 224 is a distally tapered frustaconical shaped portion at the proximal end 216 of the tubular member 202. The diameter at a proximal end 234 of the flared section 224 is larger than the diameter at a distal end 236.

The distal guide segment 205 provides for "single operator" insertion of the sheath 200 and is defined by a distal extent of the tubular member 202 so that thru lumen 230 of the tubular member 202 is also the guide lumen 209 for "single operator insertion" of the sheath 200 along a pre-inserted guide wire. The distal opening 222 defines the distal thread opening 210 of the distal guide segment 205. A side hole 238 through a side wall of the tubular member 202 is proximally spaced from the distal thread opening 210 to define the proximal thread opening 211 of the distal guide segment 205.

The distal opening 222 and the side hole 238 are spaced to provide a relatively short distal guide segment 205 which extends only along a distal portion of the sheath 200. A pre-inserted guide wire extends through guide lumen 209 (and distal thread opening 210 and proximal thread opening 211) of the distal guide segment 205 for tracking the sheath 200 along the guide wire for insertion. Since the distal guide segment 205 extends only along a relatively short distal portion of the sheath 200, the distal guide segment 205 defines means for "single operator" insertion so that a guide wire extension is not necessary.

An outer diameter of the second diameter segment 228 is smaller than the outer diameter of the first diameter segment 226. The transition portion 232 is distally tapered and is between the first diameter segment 226 and the second diameter segment 228. The flared section 224 extends from the proximal end 216 to the first diameter segment 226. The diameter of the distal end 236 of the flared section 224 coincides with the outer diameter of the first diameter segment 226. The first diameter segment 226 extends distally to the transition portion 232. The second diameter segment 228 extends from the transition portion 232 to the distal end 218 of the tubular member 202. The thru lumen 230 is sized to receive a guide wire therethrough. Preferably, the thru lumen 230 is sized to receive a single guide wire therethrough.

The peeling notch 207 is formed at the flared section 224 of the tubular member 202. The notch 208 includes a mouth 244 and a tip portion 246. The perforated extent 206 is formed by a series of slit segments 248 and connecting segments 250. The slit segments 248 are formed by a series of longitudinal cuts through the side wall 240 of the tubular member 202. The connecting segments 250 provide an uncut length of the tubular member 202 between successive slit segments 248. The perforated extent 206 extends distally from the tip portion 246 of the notch 207 to preferably the distal side hole 238 (see FIG. 13).

Marker 212 is formed of a cylindrical coil or band of radiopaque material and is mounted about the first diameter portion 226 adjacent to the distal side hole 238. Marker 214 is also formed of a cylindrical coil or band of radiopaque material and is mounted about the second diameter portion 228 at the transition portion 232. An adhesive fill 252 is used to provide a smooth transition between the outer diameter of the radiopaque marker 214 and the outer diameter of the second diameter portion 228 to eliminate an abrupt change in diameter. Preferably the adhesive fill 252 is an epoxy.

The stiffening member 208 is formed of a relatively stiff elongated cylindrical rod and is preferably designed for slidable insertion into the thru lumen 230 (at the proximal opening 220) of the elongated tubular member 202. The stiffening member 208 is long enough so that a portion of the stiffening member 208 extends outside the tubular member 202 some distance and extends through the thru lumen 230 of the tubular member 202 preferably to the side hole 238. The stiffening member 208 includes a series of distally decreasing diameter segments, preferably, a first member segment 208a, a second member segment 208b, and a third member segment 208c. The first member segment 208a has the largest outer diameter and the second and third member segments 208b and 208c have successively smaller outer diameters. Preferably, the elongated tubular member 202 is 53.2 inches (135 cm) in length. The first diameter segment 226 of the tubular member 202 is formed from a polyethylene tube having an inner diameter dimension of 0.021 to 0.025 inches (0.53 to 0.635 mm) and an outer diameter in the range of 0.028 to 0.034 inches (0.711 to 0.864 mm). Preferably, the inner diameter dimension is 0.021 inches (0.53 mm) and the outer diameter dimension is 0.028 inches (0.711 mm). The tubular member 202 may be formed of other polymer materials such as polyolefin copolymer. The tubular member 202 is preferably coated with a silicone or hydrophilic coating.

The second diameter segment 228 is formed at a distal portion of the polyethylene tube by a necking down process where the tube is drawn through a heated die. A mandrel (not shown) is used to maintain a constant inner diameter of preferably 0.021 (0.53 mm) along the necked down second diameter segment 228. The second diameter segment 228 is preferably necked down to a 0.025 inch (0.635 mm) outer diameter. The first diameter segment 226 is 53.0 inches long (134.5 cm) and the second diameter segment 228 is 0.2 inches long (5 mm) to support the radiopaque marker 214.

The flared section 224 is formed by forcing a proximal portion of the polyethylene tube over a funnel shaped die (not shown) while heat is applied to soften the tube. The softened tube assumes the flanged shape to form the flared section 224 when cooled. Preferably, the length of the frusta-conical portion is 0.25 to 0.5 inches (6.35 to 12.7 mm).

The distal side hole 238 is located 1.97 to 3.94 inches (5 to 10 cm) from the distal end 234 of the tubular member 202. As previously explained in relation to the first and second embodiments of the sheath of the invention, the distal side hole 238 is formed by a skiving process and is similarly dimensioned. The extent of the notch 208 between the mouth 244 and the tip 246 is 0.125 to 0.25 inches (3.175 to 6.35 mm). The width of the mount 244 is preferably approximately 0.021 inches (0.53 mm).

The slit segments 248 of the perforated extent 206 are substantially longer than the connecting segments 250 to facilitate the removal of the sheath 200 after use. As an example of a preferred construction for the perforated extent 206, the slit segments 248 are 10.0 inches (254.0 mm) in length and the connecting segments 250 are 0.125 inches (3.175 mm) in length. However, any suitable combination length of slit segments 248 and connecting segments 250 is contemplated for the perforated extent 206.

The stiffening member 208 is formed of stainless steel material. The length of the stiffening member 208 is approximately 55.16 inches (140 cm). In use, a portion of the stiffening member 208 always extends proximally out of the proximal opening 220 of the tubular member 202 some distance for control of the stiffening member 208. The first member segment 208a is 0.014 inches in diameter (0.355 mm). The second member segment 208b is 0.009 inches in diameter (0.23 mm). The third member segment 208c is 0.006 inches in diameter (0.15 mm). The length of the first member segment 208a is 44.66 inches (113.35 cm). The length of the second member segment 208b is 8.0 inches (20.3 cm). The length of the third member segment 208c is 2.5 inches (6.35 cm). The distally decreasing diameter segments of the stiffening member 208 provide flexibility to allow the sheath 200 (and stiffening member 208) to negotiate the vascular system of the patient. Preferably the stiffening member 208 is coated with a Teflon ® or hydrophilic polymer coating or silicone coating to provide a lubricous surface. The coating slightly increases the outer diameters of the successive member segment 208a, 208b and 208c (e.g., by 0.0004 inches and 0.01 mm).

The operation of the sheath 200 of FIGS. 12-14 is similar to that described in relation to FIGS. 6-8 and FIGS. 9-11 for the first and second embodiments of the sheath of the invention. The guide wire is separated from the tubular member 202 by pulling the two laterally apart. The wall of the tubular member 202 separates along the perforated extent 206 so the tubular member may be peeled off of the guide wire. The flared section 224 of the present embodiment facilitates the initiation of the peeling of the perforated extent 206 for removing the sheath 200 from a guide wire after use.

Figure 16:
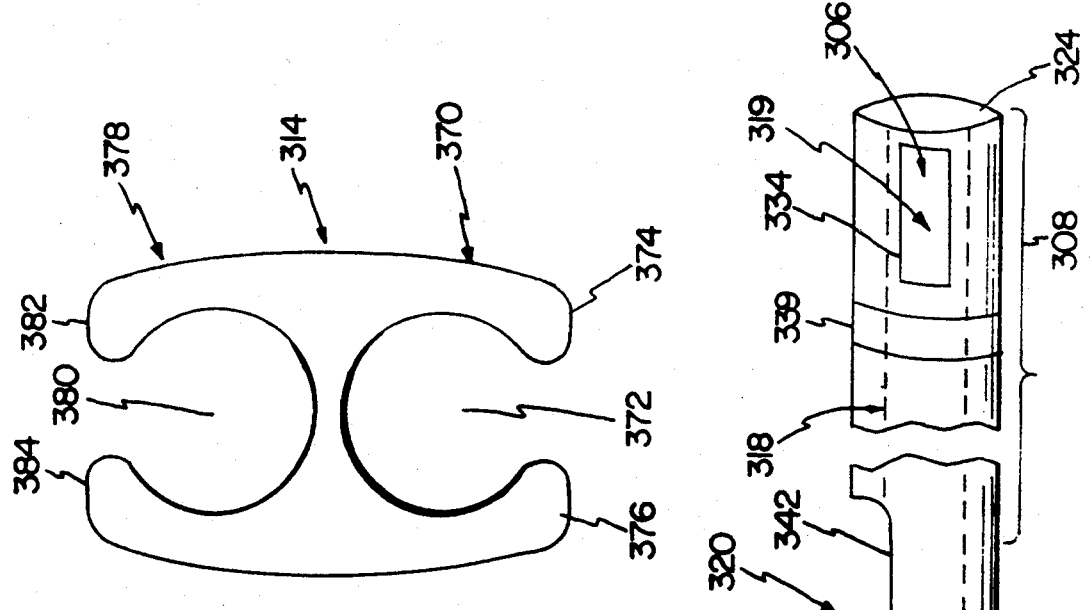
FIG. 16 is a side elevational view of a clip used with the fourth embodiment of the sheath to facilitate insertion and placement.
Figure 15:
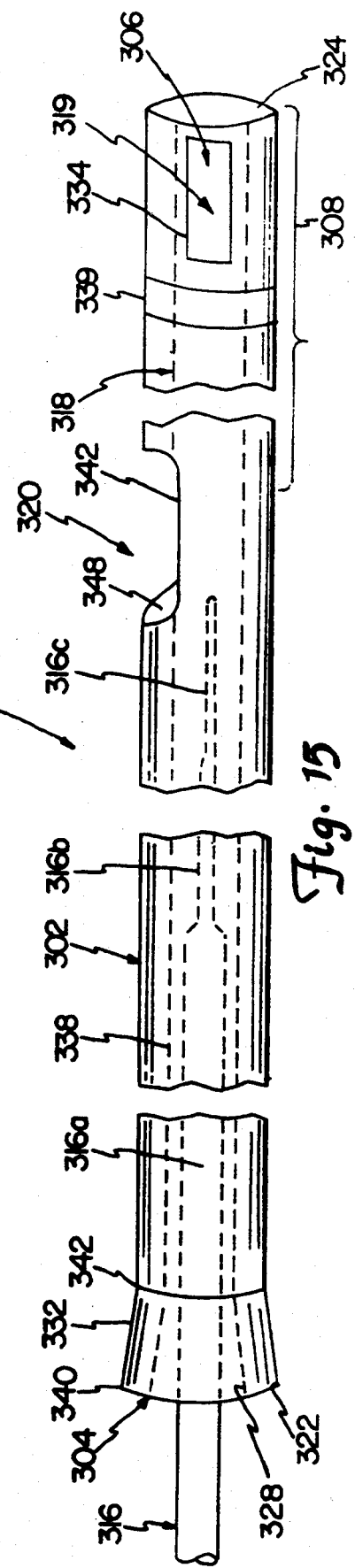
FIG. 15 is a perspective of a fourth embodiment of a sheath of the invention.

Description of the Fourth Embodiment of the Sheath of the Invention (FIGS. 15–17)

FIGS. 15–17 illustrate a fourth embodiment of the sheath 300 of the invention. As shown in FIGS. 15–17, the sheath 300 includes an elongated tubular member 302, proximal insertion opening 304, distal insertion opening 306, distal guide segment 308, longitudinal slit 310, peeling notch 312, clip 314, and stiffening member 316. The distal guide segment 308 includes a thru lumen 318, a distal thread opening 319 and a proximal thread opening 320.

The elongated tubular member 302 has a proximal end 322 and a distal end 324 and includes a proximal opening 328, a flared section 332, a longitudinal slot 334 and a single thru lumen 338. The proximal opening 328 of the tubular member 302 defines a proximal insertion opening 304 in communication with the thru lumen 338 which remains outside the patient when the sheath 300 is advanced for use. The longitudinal slot 334 extends proximally from the distal end 324 along an extent of the tubular member 302 to define the distal insertion opening 306 in communication with the thru lumen 338 of the tubular member 302. A band or coil of radiopaque material is mounted on the tubular member adjacent the slot 334, as marker 339 in FIG. 15. The tubular member 302 is preferably formed of a polyethylene material and is coated with a silicone or hydrophilic polymer coating.

The flared section 332 is a frusta-conical shaped portion at the proximal end 322 of the tubular member 302. The diameter at a proximal end 340 of the flared section 332 is larger than the diameter at a distal end 342. The diameter of the distal end 342 coincides with the outer diameter of the tubular member 302.

The distal guide segment 308 provides for "single operator" insertion of the sheath 300 and is defined by a distal extent of the tubular member 302 so that thru lumen 338 of the tubular member 302 is also the guide lumen 318 for "single operator insertion" of the sheath 300 along a pre-inserted guide wire. The longitudinal slot 334 defines the distal thread opening 319 of the distal guide segment 308. A side hole 342 through a side wall 348 of the tubular member 302 is proximally spaced from the distal thread opening 319 to define proximal thread opening 320 of the distal guide segment 308.

The longitudinal slot 334 and the side hole 342 are spaced to provide a relatively short distal guide segment 308 which extends only along a distal portion of the sheath 300. A pre-inserted guide wire extends through guide lumen 318 (and distal thread opening 319 and proximal thread opening 320) of the distal guide segment 308 for tracking the sheath 300 along the guide wire for insertion. Since the distal guide segment 308 extends only along a relatively short distal portion of the sheath 300, the distal guide segment 308 defines means for "single operator" insertion so that a guide wire extension is not necessary.

Peeling notch 312 is formed at the flared section 332 of the tubular member 302. The notch 312 includes a mouth 352 and a tip portion 354. The slit 310 is formed through the side wall 348 of the tubular member 302 and extends from the tip portion 354 of notch 312 preferably to the side hole 342 (see FIG. 17).

Figure 17A:
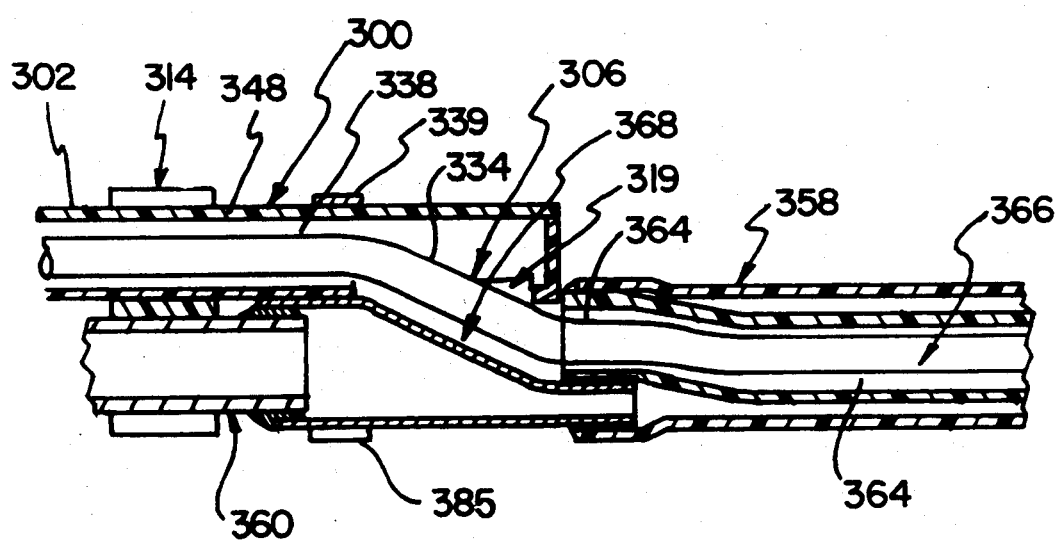
FIG. 17a is an enlarged detailed view, in cross section, of the indicated section in FIG. 17.

As previously explained as shown in FIGS. 17 and 17a, the sheath is used to facilitate a guide wire exchange for a "single operator exchange" therapeutic or diagnostic device. For example, a "single operator exchange" angioplasty balloon catheter 358 is illustrated in FIG. 17. The "single operator exchange" angioplasty device 358 includes a catheter shaft 360, a balloon 362, and a distal guide wire lumen 364. A guide wire 366 is designed to extend through a proximal opening 368 to the distal guide wire lumen 364 to facilitate placement of the "single-operator" catheter device 358. The length of the tubular member 302 of the sheath 300 is sized so that the longitudinal slot 334 aligns with the proximal opening 368 to the guide wire lumen 364 of the "single operator exchange" catheter device 358 (see FIG. 17a) while the proximal opening 328 extends outside the patient.

As shown in FIG. 16 the clip 314 is formed of a separate element designed for slidable advancement along the catheter shaft 360 to maintain the position of the sheath 300 relative thereto. The clip 314 is one piece and includes a "C" shaped catheter shaft clamp 370 having a lumen 372 and opposed flexible legs 374 and 376 and a "C" shaped sheath clamp 378 having a lumen 380 and opposed flexible legs 382 and 384.

The "C" shaped catheter shaft clamp 370 is sized so that the opposed flexible legs 374 and 376 enclose the catheter shaft 360 so that the catheter shaft 360 extends through the lumen 372 of the catheter shaft clamp 370. The lumen 372 of the catheter shaft clamp 370 is slightly larger than the catheter shaft 360 to provide a "slip-fit" between the catheter shaft clamp 370 and the catheter shaft 360 so that the catheter shaft clamp 370 is slidable along the catheter shaft 360.

The "C" shaped sheath clamp 378 is also sized so that the legs 382 and 384 engage and grip the tubular member 302. Preferably the lumen 380 is sized similar to the tubular member 302 to provide a tight fit between the sheath clamp 378 and the tubular member 302 so that clip 314 moves in combination with the tubular member 302 along the catheter shaft 360. The clip 314 is formed of a resilient thermoplastic elastomer such as polyethylene, polypropylene or Hytrel. Hytrel is a trade name for an elastomeric material of E.I. du Pont de Nemours & Co., Inc. of Delaware.

The stiffening member 316 is formed of a relatively stiff elongated cylindrical rod and is preferably designed for slidable insertion into the thru lumen 338 (at the proximal opening 328) of the elongated tubular member 302. The stiffening member 316 is long enough so that a portion of the stiffening member 316 extends outside the tubular member 302 some distance and extends through the thru lumen 230 of the tubular member 302 preferably to the distal side hole 342. The stiffening member 316 includes a series of distally decreasing diameter segments, preferably, a first member segment 316a, a second member segment 316b, and a third member segment 316c. The first member segment 316a has the larger outer diameter and the second and third member segments 316b and 316c has successfully smaller outer diameters.

Preferably the elongated tubular member 302 53.2 inches (135 cm) in length. The tubular member 302 is formed from a polyethylene tube having an inner diameter dimension of 0.021 to 0.025 inches (0.053 to 0.635 mm) and an outer diameter in the range of 0.028 to 0.034 inches (0.711 to 0.864 mm). Preferably, the inner diameter dimension is 0.021 inches (0.53 mm) and the outer diameter dimension is 0.028 inches (0.711 mm). The tubular member 302 may be formed of other polymer materials such as polyolefin copolymer. The tubular member 302 is preferably coated with a silicone type coating or hydrophilic coating.

The flared section 332 is formed by forcing a proximal portion of a polyethylene tube over a flanged shaped die (not shown) while heat is applied to soften the tube. The softened tube assumes the flanged shaped to form the flared section 332 when cooled. Preferably the length of the flared section 332 is 0.25 to 0.5 inches (6.35 to 12.7 mm). The distal side hole 342 is located 1.97 to 3.94 inches (5 to 10 cm) from the distal end 324 of the tubular member 302. As previously explained in relation to the first three embodiments of the sheath of the invention, the distal side hole 342 is formed by a skiving process and is similarly dimensioned. The extent of the notch 312 between the mouth 352 and the tip portion 354 is 0.125 to 0.25 inches (3.175 to 6.35 mm). The width of the mouth 352 is preferably approximately 0.021 inches (0.53 mm). The length of the slot 334 is 0.4 to 0.79 inches (10 to 20 mm).

The stiffening member 316 is formed of a stainless steel material. The length of the stiffening member 316 is approximately 55.16 inches (140 cm). In use, a portion of the stiffening member 316 always extends proximally out of the proximal opening 328 of the tubular member 302. The first member segment 316a is 0.014 inches in diameter (0.355 mm). The second member segment 316b is 0.009 inches in diameter (0.23 mm). The third member segment 316c is 0.006 inches in diameter (0.15 mm). The length of the first member segment 316a is 44.66 inches (113.35 cm). The length of the second member segment 316b is 8.0 inches and (20.3 cm). The length of the third member segment 316c is 2.5 inches (6.35 cm) Preferably the stiffening member 316 is coated with a teflon or hydrophilic polymer coating or silicone coating to provide a slipperier surface.

The operation of the sheath 300 of FIGS. 15-17 is similar to that described for the other three embodiments, except that prior to use of the sheath 300 the angioplasty catheter device 358 does not need to be withdrawn. The sheath 300 is mounted about a proximal end 366a of the guide wire 366 so that the guide wire 366 extends through the guide lumen 318 of the distal guide segment 308 (and through the distal thread opening 319 (defined by longitudinal slot 334) and through the proximal thread opening 320 (defined by distal side hole 342)), as shown in FIG. 17. The sheath clamp 378 of the clip 314 is tightly mounted about a distal portion of the elongated tubular member 302 distal of the side hole 342. The catheter shaft clamp 370 of clip 314 is slidably mounted about a proximal end of the catheter shaft 360.

The distal guide segment 308 is advanced distally along the guide wire 366 while the catheter shaft clamp 370 of clip 314 is slid along the catheter shaft 360 to advance the sheath 300 into the patient's vasculature. The sheath 300 is advanced until the distal insertion opening 306 (longitudinal slot 334) aligns with the proximal opening 368 to the guide wire lumen 364 as shown most clearly in FIG. 17a. The tight fit of the sheath clamp 378 of the clip 314 with the tubular member 302 and the "slip-fit" of the catheter shaft clamp 370 of clip 314 with the catheter shaft 360 facilitates placement of the sheath 300.

Ideally the catheter device 358 will have a radiopaque marker (such as marker 385) adjacent its proximal opening 368, so an operator can align the sheath 300 and catheter device 358 via alignment of their respective markers 339 and 385. After the sheath 300 is inserted and the longitudinal slot 334 is aligned with the proximal opening 368 of the guide wire lumen 364 as shown in FIG. 17a, the guide wire 366 is proximally withdrawn from the patient (and from within the lumens of the "single operator exchange" angioplasty device 358 and sheath 300).

A distal tip of the withdrawn guide wire may be reshaped or a substitute guide wire may be used to continue treatment. The substitute or reshaped guide wire is inserted into the patient via the guide wire sheath 300 and the distal guide wire lumen 364 of the "single operator exchange" catheter device 358. The substitute or reshaped guide wire is inserted through the proximal insertion opening 304 and advanced through the thru lumen 338 and distal insertion opening 306 (defined by longitudinal slot 334) of the sheath 300. Fluoroscopy or proximal markers are used to indicate when the distal tip of the guide wire is at the proximal opening 368 of the catheter device 358. The substitute guide wire is advanced through the longitudinal slot 334 laterally into the proximal opening 368 to the guide wire lumen 364 and advanced until the guide wire extends beyond a distal end of the "single operator exchange" catheter device 358. After the guide wire is inserted in this way, the sheath 300 may be withdrawn by peelably removing the exchange sheath along the slit 310 to remove the sheath 300 from the inserted guide wire. The clip 314 facilitates the insertion of the sheath 300 relative to the catheter shaft 360 of the "single operator exchange" catheter device 358 and further assures that the distal insertion opening 306 (slot 334) aligns with the proximal opening 368 to the guide wire lumen 364.

Conclusion

The sheath of the present invention provides an effective sheath for performing a guide wire exchange for a "single operator exchange" diagnostic or therapeutic device or for performing a guide wire exchange for a guide wire which is inserted alone and does not extend through a guide wire lumen of an "over-the-wire" type therapeutic or diagnostic device. Several alternative embodiments of the sheath for intravascular treatment of the present invention are illustrated herein. Various combinations of these alternative component and catheter structures are contemplated and are intended to be considered although not explicitly shown or discussed. For example, each embodiment can be modified to include a flared proximal end, and the need for separating the tubular member wall to allow peel away of the guide wire are interchangeable among the embodiments. These illustrations are merely examples and are not intended to be limitations on the possible combinations of the features and concepts disclosed herein for a sheath adapted for use in exchanging one guide member for the same or another guide member.

Although the present invention has been described with reference to preferred embodiments, workers skilled in the art will recognize that changes may be made in form and detail without departing from the spirit and scope of the invention. Also, it should be understood that the invention is not strictly limited by the specific uses set forth herein and the scope of the invention should not be limited thereby.

What is claimed is:

1. A sheath for use in exchanging one guide member for the same or another guide member, wherein each guide member is adapted to be inserted into a patient's vasculature so that a distal portion of the guide member is within the patient and a proximal portion thereof remains outside the patient, the sheath comprising:

an elongated tubular member having a single longitudinally extending lumen sized to slidably receive a guide member therein, the tubular member having a distal insertion opening in communication with the lumen adjacent its distal end, a proximal insertion opening in communication with the lumen adjacent its proximal end, and having, closer to its distal end than its proximal end, a distal side hole in communication with the lumen, and the tubular member being sized so that when advanced into a patient's vasculature over the guide member, the proximal insertion opening remains outside the patient;

means for peelably removing at least a portion of the tubular member from a guide member extending through the lumen, the means permitting separation of the portion of the tubular member from the guide member outside the patient as the tubular member is proximally withdrawn from the patient's vasculature while the guide member remains generally stationary therein, the removing means extending from the distal side hole to the proximal end of the tubular member;

means for stiffening the tubular member defined by a relatively stiff elongated element which is sized for slidable insertion into the lumen of the tubular member at the proximal end thereof, the stiffening member being independent of the guide member; and a clip for securing the tubular member relative to a shaft of a single operator exchange intravascular dilatation catheter, the clip being fixedly secured to the tubular member and being slidably connectable to the shaft of the intravascular catheter to maintain the tubular member and the shaft of the intravascular catheter in a side by side relationship.

2. The sheath of claim 1 wherein the means for peelably removing the tubular member from the guide member comprises:

a slit through a side wall of the tubular member, the slit extending along the tubular member distally from the proximal insertion opening.

3. The sheath of claim 1 wherein the means for peelably removing the tubular member from the guide member comprises a tearable extent.

4. The sheath of claim 3 wherein the tearable extent is formed of a longitudinally extending area of reduced wall thickness of the tubular member.

5. The sheath of claim 3 wherein the tearable extent is formed by heating a longitudinal extent of the tubular member to weaken the tubular member.

6. The sheath of claim 1 wherein the means for peelably removing the tubular member from the guide member comprises a tubular member formed of a tearable material.

7. The sheath of claim 1 wherein the means for peelably removing the tubular member from the guide member comprises:

a perforated extent extending along the tubular member distally from the proximal insertion opening, the perforated extent including a series of slit segments and connecting segments, the slit segments being formed of cuts through a side wall of the tubular member.

8. The sheath of claim 1 wherein the elongated element of the stiffening means is distally tapered.

9. The sheath of claim 1 wherein the proximal insertion opening is defined by a proximal end hole forming the proximal end of the tubular member.

10. The sheath of claim 9 and further including a notch at the proximal end of the tubular member to facilitate the initiation of the separation of the tubular member from the guide member.

11. The sheath of claim 10 wherein the tubular member has a flared section at its proximal end.

12. The sheath of claim 1 wherein the proximal insertion opening is defined by a proximal side hole in the tubular member which is spaced distally from the proximal end of the tubular member.

13. The sheath of claim 1 wherein tile distal insertion opening is defined by a distal end hole forming the distal end of the tubular member.

14. The sheath of claim 1 wherein the distal insertion opening is defined by a longitudinal slot extending proximally from the distal end of the tubular member along an extent of the tubular member.

15. The sheath of claim 1 wherein the tubular member has a length so that when positioned side by side with a single operator exchange intravascular dilatation catheter inserted into a patient's vasculature, the distal insertion opening is alignable laterally adjacent a proximal opening to a guide member lumen of a single operator exchange intravascular dilatation catheter when the proximal insertion opening of the tubular member remains outside the patient.

16. A method for removing a guide wire pre-inserted into a patient and inserting a guide wire comprising the steps of:

providing a sheath comprising an elongated tubular member having a proximal insertion opening, a distal insertion opening and a single through lumen therethrough sized to receive a guide wire, the proximal and distal insertion openings being in communication with the through lumen and the sheath having a distal guide segment at its distal end which has a guide lumen and a proximal thread opening and a distal thread opening in communication with the guide lumen;

inserting a stiffening member into the through lumen of the tubular member prior to inserting the sheath into the patient, the stiffening member being independent of the guide wire and formed of a relatively stiff elongated element sized for slidable insertion into the through lumen of the tubular member, inserting a proximal end of the guide wire pre-inserted into the patient through the distal thread opening and the proximal thread opening into the guide lumen of the distal guide segment of the sheath;

advancing the sheath distally along the pre-inserted guide wire until the distal end of tubular member is in a desired position relative to a distal end of the pre-inserted guide wire;

withdrawing the pre-inserted guide wire proximally from the distal guide segment through the proximal thread opening and the distal thread opening;

withdrawing the stiffening member from the through lumen of the tubular member;

inserting a guide wire through the proximal insertion opening and advancing the guide wire through the single through lumen until a distal end of the guide wire is in a desired position; and withdrawing the sheath from the patient while peelably removing the tubular member from the guide wire and initiating the removing of the tubular member from the guide wire at the proximal end of the sheath.

17. The method of claim 16 and further comprising the step of:

withdrawing an intravascular device inserted into the patient from its position over the pre-inserted guide wire in the patient prior to inserting and advancing the sheath.

18. A method for removing a pre-inserted guide wire extending through a guide wire lumen of a single operator exchange intravascular dilatation catheter inserted into a patient and inserting a guide wire into the guide wire lumen of the single operator exchange intravascular dilatation catheter in the patient, comprising the steps of:

providing a sheath comprising an elongated tubular member having a proximal insertion opening, a distal insertion opening and a single through lumen therethrough sized to receive a guide wire, the proximal and distal insertion openings being in communication with the through lumen and the sheath having a distal guide segment at its distal end which has a guide lumen and a proximal thread opening and a distal thread opening in communication with the guide lumen, the distal thread opening being disposed 90° about the periphery of the tubular member, and spaced longitudinally, relative to the proximal thread opening;

inserting a stiffening member into the proximal insertion opening at the proximal end and the through lumen of the tubular member prior to inserting the sheath into the patient, the stiffening member being independent of the guide wire and formed of a relatively stiff elongated element sized for slidable insertion into the through lumen of the tubular member;

inserting a proximal end of the pre-inserted guide wire through the distal thread opening and the proximal thread opening into the guide lumen of the distal guide segment of the tubular member;

advancing the sheath distally along the pre-inserted guide wire in a side by side relationship with the intravascular dilatation catheter until the distal insertion opening of the tubular member is aligned laterally adjacent to and facing a proximal opening to the guide wire lumen of the single operator exchange intravascular dilatation catheter;

withdrawing the pre-inserted guide wire proximally from the distal guide segment of the intravascular catheter through the proximal thread opening and the distal thread opening of the tubular member;

withdrawing the stiffening member from the through lumen of the tubular member;

inserting a guide wire through the proximal insertion opening and advancing the guide wire through the single through lumen until a distal end of the guide wire extends through the distal insertion opening into the guide wire lumen of the single operator exchange intravascular catheter; and withdrawing the sheath from the patient while peelably removing the tubular member from the guide wire and initiating the removing of the tubular member from the guide wire at the proximal end of the sheath.

19. The method of claim 18 wherein the advancing step includes:

maintaining a portion of the sheath in a coupled relation to the single operator exchange intravascular device.

20. The method of claim 18 wherein immediately following the step of inserting the preinserted wire through the distal thread opening, and prior to the step of advancing the sheath, the method further includes the step of:

fixing a clip to the tubular member between its distal thread opening and its proximal thread opening and coupling the clip to the dilatation catheter so that the clip is slidably movable longitudinally along the dilatation catheter to maintain the tubular member and dilatation catheter in a side by side relationship while permitting sliding longitudinal movement of the tubular member relative to the dilatation catheter.

21. A sheath system for use in exchanging one guide member for the same or another guide member, wherein each guide member is adapted to be inserted into a patient's vasculature so that a distal portion of the guide member is within the patient and a proximal portion thereof remains outside the patient, the sheath system comprising:

an elongated tubular member having a single longitudinally extending lumen sized to slidably receive a guide member therein, the tubular member having a distal insertion opening in communication with the lumen adjacent its distal end, a proximal insertion opening in communication with the lumen adjacent its proximal end, and having, closer to its distal end than its proximal end, a distal side hole in communication with the lumen, and the tubular member being sized so that when advanced into a patient's vasculature over the guide member, the proximal insertion opening remains outside the patient;

means for peelably removing at least a portion of the tubular member from a guide member extending through the lumen, said means permitting separation of said portion of the tubular member from the guide member outside the patient as the tubular member is proximally withdrawn from the patient's vasculature while the guide member remains generally stationary therein; and means for securing the tubular member relative to a shaft of a single operator exchange intravascular dilatation catheter, the securing means having a first portion fixed to the tubular member between the distal insertion opening and the distal side hole of the tubular member and having a second portion slidably connectable to the shaft of the intravascular catheter, the securing means maintaining the intravascular catheter and tubular member in side by side relationship while permitting longitudinal sliding movement of the tubular member relative to the shaft of the intravascular catheter.

22. A sheath for use with a single operator exchange dilatation catheter in exchanging one guide member for the same or another guide member, wherein the intravascular catheter extends within a patient and is of the type having a guide member lumen in a distal portion thereof, the guide member lumen having a proximal opening in communication with the guide member lumen and wherein each guide member is adapted to be inserted into a patient's vasculature so that a distal portion of the guide member is within the patient and is adapted for insertion within the proximal guide member lumen opening of the intravascular catheter and a proximal portion of the guide member remains outside the patient, the sheath comprising:

an elongated tubular member having a single longitudinally extending lumen sized to slidably receive a guide member therein, the tubular member having a distal insertion opening in communication with the lumen adjacent a closed distal end, a proximal insertion opening in communication with the lumen at its proximal end, and having, closer to its distal end than its proximal end, a distal side hole in communication with the lumen, the distal insertion opening being defined by a longitudinal slot extending proximally from the distal end of the tubular member along an extent of the tubular member, and the distal side hole being disposed at an angle about the periphery of the tubular member relative to the longitudinal slot of the distal insertion opening and being spaced longitudinally relative to the distal insertion opening, the tubular member being sized so that when advanced into a patient's vasculature over the guide member, the proximal insertion opening remains outside the patient; and means for peelably removing at least a portion of the tubular member from a guide member extending through the lumen, said means permitting separation of said portion of the tubular member from the guide member outside the patient as the tubular member is proximally withdrawn from the patient's vasculature while the guide member remains generally stationary therein, the removing means extending from the distal side hole to the proximal end of the tubular member.

23. A sheath system for use in exchanging one guide member for the same or another guide member, wherein each guide member is adapted to be inserted into a patient's vasculature so that a distal portion of the guide member is within the patient and a proximal portion thereof remains outside the patient, the sheath system comprising:

an elongated tubular member having a single longitudinally extending lumen sized to slidably receive a guide member therein, the tubular member having a distal insertion opening in communication with the lumen adjacent its distal end, a proximal insertion opening in communication with the lumen adjacent its proximal end, and having, closer to its distal end than its proximal end, a distal side hole in communication with the lumen, and the tubular member being sized so that when advanced into a patient's vasculature over the guide member, the proximal insertion opening remains outside the patient, wherein the proximal insertion opening is defined by a proximal end hole forming the proximal end of the tubular member and the distal insertion opening is defined by a longitudinal slot extending proximally from the distal end of the tubular member along an extent of the tubular member;

means for peelably removing at least a portion of the tubular member from a guide member extending through the lumen, said means permitting separation of said portion of the tubular member from the guide member outside the patient as the tubular member is proximally withdrawn from the patient's vasculature while the guide member remains generally stationary therein, the removing means extending from the distal side hole to the proximal end and including a notch and flared section at the proximal end of the tubular member to facilitate the initiation of the separation of the tubular member from the guide member;

means for stiffening the tubular member defined by a relatively stiff elongated element which is sized for slidable insertion into the lumen of the tubular member at the proximal end thereof; and a clip for securing the tubular member relative to a shaft of a single operator exchange intravascular dilatation catheter, the clip being fixed to the tubular member and being slidably connectable to the shaft of the intravascular catheter to maintain the tubular member and shaft of the intravascular catheter in a side by side relationship while permitting the tubular member to slide longitudinally relative to the intravascular catheter.

24. An angioplasty system for use in exchanging one guide for the same or another guide wire, comprising:

an intravascular dilatation catheter of a type wherein the catheter has a guide wire lumen in a distal portion thereof with a proximal guide wire lumen opening communicating with the guide wire lumen, and further in which the proximal guide wire lumen opening is located through a side wall of the intravascular catheter substantially distal of a proximal end of the intravascular catheter;

a guide wire adapted to be inserted into a patient's vasculature so that a distal portion of the guide wire is within the patient and a proximal portion thereof remains outside the patient;

a sheath comprising an elongated tubular member having a single longitudinally extending lumen sized to slidably receive a guide wire therein, the tubular member having a distal insertion opening in communication with the lumen adjacent its distal end, a proximal insertion opening in communication with the lumen adjacent its proximal end, and having, closer to its distal end than its proximal end, a distal side hole in communication with the lumen, and the tubular member being sized so that when advanced into a patient's vasculature over the guide wire, the proximal insertion opening remains outside the patient;

means for peelably removing at least a portion of the tubular member from a guide wire extending through the lumen, said means permitting separation of the portion of the tubular member from the guide wire outside the patient as the tubular member is proximally withdrawn from the patient's vasculature while the guide wire remains generally stationary therein, the removing means extending from the distal side hole to the proximal end of the tubular member;

means for stiffening the tubular member defined by a relatively stiff elongated element which is sized for slidable insertion into the lumen of the tubular member at the proximal end thereof; and means for securing the tubular member relative to a shaft of the intravascular dilatation catheter, the securing means having a first portion fixed to the tubular member between the distal insertion opening and the distal side hole of the tubular member and having a second portion capable of being slidably connected to the shaft of the intravascular dilatation catheter, the securing means maintaining the intravascular dilatation catheter and tubular member in side by side relationship while permitting longitudinal sliding movement of the tubular member relative to the shaft of the intravascular dilatation catheter.

25. The system of claim 24 wherein tubular member has a length so that with proximal end of the tubular member extending outside the patient, the distal side hole is alignable laterally adjacent to the proximal guide wire lumen opening of intravascular catheter to permit passage of guide wire between the tubular member and the catheter.

* * * * *